(12) United States Patent
Poulain et al.

(10) Patent No.: US 8,193,333 B2
(45) Date of Patent: Jun. 5, 2012

(54) CANCER THERAPY USING BCL-X$_L$-SPECIFIC SINA

(75) Inventors: Laurent Poulain, Bretteville l'Orgueilleuse (FR); Pascal Gauduchon, Plumetot (FR); Emilie Brotin, Caen (FR); Ester Saison-Behmoaras, Paris (FR)

(73) Assignee: Centre Regional de Lutte Contre le Cancer-Centre Francois Baclesse (FR)

( * ) Notice: Subject to any disclaimer, the term of this patent is extended or adjusted under 35 U.S.C. 154(b) by 0 days.

(21) Appl. No.: 12/306,093

(22) PCT Filed: Jun. 22, 2007

(86) PCT No.: PCT/IB2007/002762
§ 371 (c)(1),
(2), (4) Date: Jun. 8, 2009

(87) PCT Pub. No.: WO2008/001219
PCT Pub. Date: Jan. 3, 2008

(65) Prior Publication Data
US 2009/0312393 A1 Dec. 17, 2009

(30) Foreign Application Priority Data
Jun. 26, 2006 (WO) .................. PCT/IB2006/002685

(51) Int. Cl.
*C07H 21/04* (2006.01)
*C07H 21/02* (2006.01)
*A61K 48/00* (2006.01)

(52) U.S. Cl. .................. 536/24.5; 536/23.1; 514/44
(58) Field of Classification Search .................. None
See application file for complete search history.

(56) References Cited

U.S. PATENT DOCUMENTS
7,632,824 B2 * 12/2009 Freier .................. 514/44 R
2006/0166920 A1 7/2006 Xu et al.

FOREIGN PATENT DOCUMENTS
WO WO 00/01393 1/2000
WO WO 2000/001393 A2 * 1/2000
WO WO 2006/099667 9/2006
WO WO 2008/01156 1/2008

OTHER PUBLICATIONS

Bertrand et al. (Biochemical and Biophysical Research Communications, 296, 2002, pp. 100-1004).*
Elbashir et al. (The EMBO Journal, vol. 20, No. 23, 2001, pp. 6877-6888).*
International Search Report for PCT/IB2007/002762 filed Jun. 22, 2007.
Dodier et al: "Bcl-XL is functionally non-equivalent for the regulation of growth and survival in human ovarian cancer cells"; Gynecologic Oncology; vol. 100, No. 2, Feb. 2006, pp. 254-263; XP005234850.
Kanda Kayoko et al.: "Enhanced apoptosis to chemotherapeutic agents is dependent on NF kappa B and Bcl2-related proteins but is independent of p53 and bas in Burkitt's lymphoma cells"; Blood; vol. 104, No. 11, Part 1; Nov. 2004; XP008075422.
Liu Fang et al.: "RNA interference by expression of short hairpin RNAs suppresses bcl-xL gene expression in nasopharyngeal carcinoma cells"; Acta Pharmacolica Sinica; vol. 26, No. 2, Feb. 2005; pp. 228-234; XP002421385.
Hon Huiming et al: "bcl-X-L is critical for dendritic cell survival in vivo"; Journal of Immunology; vol. 173, No. 7, Oct. 2004; pp. 4425-4432; XP002421386.
Lei Xiao-Yong et al: "Silencing of Bcl-XL expression in human MGC-803 gastric cancer cells by siRNA"; Acta Biochimica et Biophysica Sinica; vol. 37, No. 8; Aug. 2005; pp. 555-560; XP002421387.
Taniai Makiko et al: "Mcl-l meidates tumor necrosis factor-related apoptosis-inducing ligand resistance in human cholangiocarcinoma cells", Cancer Research; vol. 64, No. 10; May 15, 2004; pp. 3517-3524; XP002421388.

* cited by examiner

*Primary Examiner* — Amy Bowman
(74) *Attorney, Agent, or Firm* — Alston & Bird LLP

(57) ABSTRACT

The invention relates to a double-stranded short interfering nucleic acid (siNA) molecule specific to the Bcl-X$_L$ transcript, comprising a sense and an antisense region, wherein the sense region comprises the nucleotide sequence SEQ ID NO: 1 or a sequence having at least 70% identity, preferably at least 80% identity, more preferably at least 90% identity with said sequence, and the antisense region comprises a nucleotide sequence that is complementary to the sense region, and its use for treating cancer.

24 Claims, 16 Drawing Sheets

A

B

A

B

CANCER THERAPY USING BCL-X$_L$-SPECIFIC SINA

CROSS REFERENCE TO RELATED APPLICATIONS

This application is a national stage application filed under 35 U.S.C. 371 of International Application No. PCT/IB2007/002762, filed Jun. 22, 2007, which claims priority from International Application No. PCT/IB2006/002685, filed Jun. 26, 2006.

FIELD AND BACKGROUND OF THE INVENTION

The invention relates to short nucleic acid molecules specific to the the Bcl-X$_L$ mRNA that down-regulate the expression of the Bcl-X$_L$ protein by RNA interference and inhibit the growth of tumor cells in vivo, and to their use for cancer therapy.

Apoptosis is regulated in part by the Bcl-2 protein family, including pro-apoptotic Bax, Bcl-X$_S$, Bak, Bad, Bid, Bik, Bim, and anti-apoptotic Bcl-2, Bcl-X$_L$, Mcl-1, A1 and Bcl-W. The susceptibility of cells to apoptosis induced by various stimuli such as cytotoxic drugs, serum starvation and radiations appears to be determined, at least in part, by the subcellular localization and the relative ratio between pro- and anti-apoptotic proteins, which can heterodimerize and titrate one another's function (White, E., Genes Dev., 1996, 10, 1-15; Korsmeyer, S. J., Cancer Res., 1999, 59, 1693s-1700s; Cory, S. and Adams, J. M., Nat. Rev. Cancer, 2002, 2, 647-656).

High expression levels of anti-apoptotic members of Bcl-2 family have been found in many tumors, and up regulation of Bcl-2 and Bcl-X$_L$ has been shown to be a key element in malignancy and drug resistance (Reed, J. C., Semin. Hematol., 1997, 34, 9-19; Konopleva et al., Br. J. Haematol., 2002, 118, 521-534; Lebedeva et al., Cancer Res., 2000, 60, 6052-6060; Liu et al., Gynecol. Oncol., 1998, 70, 398-403; Simonian et al., Blood, 1997, 90, 1208-1206). In particular, Bcl-2 and/or Bcl-X$_L$ are frequently overexpressed in ovarian, nasopharyngeal, breast, prostate and colon carcinoma, glioma, mesothelioma, and melanoma (He et al., Chin. J. Cancer, 2003, 22, 11-15; Min et al, Chin. J. Oncol., 2004, 26, 14-16; Krishna et al., J. Neurosurg., 1995, 83, 1017-1022; Kajewski et al., Am. J. Pathol., 1997, 150, 805-814; Cao et al., Am. J. Respir. Cell. Biol., 2001, 25, 562-568; Soini et al., Clin. Cancer Res., 1999, 5, 3508-3515; Kojima et al., J. Biol. Chem., 1998, 273, 16647-16650; Olopade et al., Cancer J. Sci. Am., 1997, 3, 230-237; Zapata et al, Breast Cancer Res. Treat., 1998, 47, 129-140; Simonian et al., Blood, 1997, 90, 1208-1216; Leiter et al., Arch. Dermatol. Res., 2000, 292, 225-232; Nicholson et al., Nature, 2000, 407, 810-816; Krajewska et al., Cancer Res., 1996, 56, 2422-2427; Maurer et al., Dig. Dis. Sci., 1998, 43, 2641-2648; Mercatante et al., J. Biol. Chem., 2002, 277, 49374-49382; Ferrandina et al., Cancer Lett., 2000, 155, 19-27; Liu et al., Gynecol. Oncol., 1998, 70, 498-503; Marone et al, Clin. Cancer Res., 1998, 4, 517-524; French Patent Application FR 0108864). However, Bcl-X$_L$ is generally considered more efficient than Bcl-2 to suppress apoptosis induced by cytotoxic drugs and radiations (Simonian et al, precited; Gottschalk et al., P.N.A.S., 1994, 91, 7350-7354). Therefore Bcl-X$_L$ represents a good target for cancer therapy, especially for cancers resistant to conventional anticancer agents.

Transcription of the BCL2L1 gene (BCL2-like 1, BCL2L, BCLX, Bcl-X, bcl-x, or BCL-X gene) produces alternatively spliced variants encoding three isoforms: the longer anti-apoptotic isoform (Bcl-X$_L$), the shorter pro-apoptotic isoform (Bcl-X$_S$) and a Bcl-X (beta isoform).

Bcl-X$_L$ is a 233 amino acids protein encoded by the longer transcript variant (transcript variant 1) comprising Exon 1, Exon 2 and Exon 3 of the BCL2L1 gene: the human Bcl-X$_L$ mRNA and protein correspond to NCBI accession numbers NP_612815 (SEQ ID NO: 3) and NM_138578 (SEQ ID NO: 2), respectively.

Bcl-X$_S$ is a 170 amino acids protein having the N-terminal sequence (positions 1 to 125) and the C-terminal sequence (positions 189 to 233) of the Bcl-X$_L$ protein but lacking a 63 amino acids sequence from positions 126 to 188 of the Bcl-X$_L$ protein. Bcl-X$_S$ is encoded by the shorter transcript variant (transcript variant 2) comprising Exon 1, the 5' sequence of Exon 2 and Exon 3. Bcl-X$_S$ mRNA lacks the 189 nucleotides sequence located at the 3' end of Exon 2, that is specific to the Bcl-X$_L$ transcript. Also, the corresponding 63 amino acids sequence of the Bcl-X$_L$ protein, which is missing in Bcl-X$_S$, is specific to Bcl-X$_L$ protein. The human Bcl-X$_S$ mRNA and protein correspond to NCBI accession numbers NP_001182 and NM_001191, respectively.

Bcl-X (beta) is a 227 amino acids protein having the N-terminal sequence of Bcl-X$_L$ (positions 1 to 188 of Bcl-X$_L$ protein, encoded by Exon 1 and Exon 2 of the BCL2 gene), and a C-terminal sequence of 39 amino acids, encoded by Intron 2 of the BCL2 gene.

The Bcl-X$_L$ is located at the outer mitochondrial membrane and appears to regulate cell death by blocking the releases of the caspase activator and cytochrome c, from the mitochondrial membrane (Desagher S. and Martinou, J. C., Trends Cell. Biol., 2000, 10, 369-377; Hengartner, M. O., Nature, 2000, 407, 770-776; Kroemer, G., Nat. Med., 1997, 3, 614-620 ; Kroemer et al., Immunol. Today, 1997, 18, 44-51; Marchetti et al., J. Exp. Med., 1996, 184, 1155-1160; Minn et al., Nature, 1997, 385, 353-357; Susin et al., J. Exp. Med., 1996, 184, 1331-1341).

Down-regulation of Bcl-X$_L$ expression by antisense oligonucleotides was shown to induce apoptosis and to potentiate the cytotoxic effect of chemotherapy on cancer cells (US Patent Application US 2003/0191300; U.S. Pat. Nos. 5,776, 905 and 6,143,291; International PCT Applications WO 00/01393, WO 00/66724; Lebedeva et al., precited ; Yang et al., The J. Biochem., 2003, 278, 25872-25878; Sonnenmann et al., Cncer Letters, 2004, 209, 177-185; Sonnenmann et al., Int. J. Oncol., 2004, 25, 1171-1181; Ozvaran et al., Mol. Cancer Therapeutics, 2004, 3, 545-550; Smythe et al., The J. Thoracic and Cardiovascular Surgery, 2002, 123, 1191-1198; Simoes et al., Int. J. Cancer, 2000, 87, 582-590, Hopkins-Donaldson et al., Int. J. Cancer, 2003, 106, 160-166; Heeres et al., Int. J. Cancer, 2002, 99, 29-34; Taylor et al., Oncogene, 1999, 18, 4495-4504; Wacheck et al., British Journal of Cancer, 2003, 89, 1352-1357; Taylor et al., Nature Biotechnology, 1999, 17, 1097-1100; Mercatante et al., precited; Frankel et al., Cancer Research, 2001, 61, 4837-4841; Roy et al., Oncogene, 2000, 19, 141-150). However, antisense oligonucleotide technology faces many problems including low absorption rates, non-specific inhibition effects, large effective dosage and toxicity.

The successful use of small interfering RNAs (siRNAs) technology for inhibiting the expression of a specific target holds great promise for the development of new treatment for cancer.

RNAi interference is the process where the introduction of double-stranded RNA into a cell inhibits gene expression in a sequence dependent fashion (reviewed in Shuey et al., Drug Discovery Today, 2002, 7, 1040-1046). RNAi has been observed in a number of organisms such as mammalian, Drosophila, nematodes, fungi and plants and is believed to be involved in anti-viral defense, modulation of transposon-activity and regulation of gene expression. RNAi is usually described as a post-transcriptional gene-silencing mechanism in which dsRNA triggers degradation of homologous messenger RNA in the cytoplasm. Target recognition is highly sequence specific since one or two base pair mismatches between the siRNA and the target gene will greatly reduce silencing effect. The mediators of RNA interference are 21-and 23-nucleotide small interfering RNAs (siRNA). In a second step, siRNAs bind to a ribonuclease complex called RNA-induced silencing complex (RISC) that guides the small dsRNA to its homologous mRNA target. Consequently, RISC cuts the mRNA approximately in the middle of the region paired with the antisens diRNA, after which the mRNA is further degraded.

Administration of siRNA to mice was shown to inhibit efficiently the expression of a target located in various organs (liver, brain, eyes, lung, kidney) as well as in xenografts (Braasch et al., Biochemistry, 2003, 42, 7967-7975; Duxbury et al., Biochem. Biophys., Res. Comm., 2003, 311, 786-792; Giladi et al., Mol. Ther., 2003, 8, 769-776; Lewis et al., Nat. Genet., 2002, 32, 107-108; Makimura et al, BMC Neurosci., 2002, 3, 18-; Reich et al., Mol. Vis., 2003, 9, 210-216; Song et al., Nat. Med., 2003, 9, 347-351; Zender et a., P.N.A.S., 2003, 100, 7797-7802.

Compared with antisense technology, RNAi is an efficient gene-specific technology, and has advantages of long-term stability, reversibility, and simple procedures.

RNAis targeting Bcl-$X_L$ have been used, in vitro to study the role of Bcl-$X_L$ in cell survival and resistance to chemotherapy. Down-regulation of Bcl-$X_L$ expression by RNAi was shown to induce apoptosis and to potentiate the cytotoxic effect of chemotherapy on cancer cells, in vitro (Taniai et al., Cancer Res., 2004, 64, 3517-3524; Zhang et al., Haematologica, 2004, 89, 1199-1206; Zender et al., Hepatology, 2005, 41, 280-288; Shimizu et al., Nature Cell Biology, 2004, 6, 1221-1228; Hon et al., J. Immunol., 2004, 173, 4425-4432; Dodier et al, Gynecologic Oncology, Epub, Sep. 26, 2005; He et al., Chinese J. Cancer, 2005, 24, 646-652; Liu et al., Acta Pharmacol., Sin., 2005, 26, 228-234; Lei et al., Acta Biochimica et Biophysica Sinica, 2005, 37, 555-560; Pizzi et al., Cell Death and Differenciation, 2005, 12, 761-772; Rorhbach et aL., J. Mol. Cell. Cardio., 2005, 38, 485-493; Tran et al., The J. Biol., Chem., 2005, 280, 3483-3492; Zhu et al., Cancer Biology and Therapy, 2005, 4, 393-397; Zhu et al., Molecular Cancer Therapeutics, 2005, 4, 451-456; US Patent Application 2005/0176025).

However, few RNAis are specific to Bcl-$X_L$ (Zender et al.; Hon et al.; Dodier et al.; He et al., Liu et al., Tran et al., Zhu et al., Cancer Biology and Therapy, precited). Furthermore, some of the Bcl-XL-specific siRNAis have been tested only in combination with non-specific siRNAis (Dodier et al. precited) and none of the Bcl-$X_L$-specific siRNAis was proven to have an antitumoral effect in vivo.

SUMMARY OF THE INVENTION

The inventors have engineered Bcl-$X_L$-specific siRNA able to down-regulate efficiently the expression of the anti-apoptotic protein Bcl-$X_L$. Injection of low dose of the Bcl-$X_L$-specific siRNA to mice implanted with human chemoresistant tumor cells increases considerably the mice survival and induces a complete regression of the pre-established tumor for at least 5 months after tumor cells implantation.

This siRNA is useful in cancer therapy, in particular for treating tumors which are resistant to conventional anticancer agents.

Therefore, the invention relates to a double-stranded short interfering nucleic acid (siNA) molecule specific to the Bcl-$X_L$ transcript, comprising a sense and an antisense region, wherein the sense region comprises the nucleotide sequence SEQ ID NO: 1 or a sequence having at least 70% identity, preferably at least 80% identity, more preferably at least 90% identity with said sequence, and the antisense region comprises a nucleotide sequence that is complementary to the sense region.

Definitions

"short nucleic acid molecule" refers to a nucleic acid molecule no more than 100 nucleotides in length, preferably no more than 80 nucleotides in length, and most preferably, no more than 50 nucleotides in length. siNA are usually between 15 to 50 nucleotides in length, preferably, between 15 and 40 nucleotides, more preferably, between 15 and 30 nucleotides in length.

"interfering nucleic acid molecule" refers to a nucleic acid molecule capable of mediating RNA interference.

"RNA interference" (RNAi) refers to the process of sequence specific post-transcriptional gene silencing, induced by introduction of duplexes of synthetic short nucleic acid molecule in cells, for example duplexes of synthetic 21-nucleotide RNAs, as first described by Elbashir et al., Nature 2001, 411, 494- and in the International PCT Application WO 01/75164.

"nucleotide" refers to standard ribonucleotides and deoxyribonucleotides including natural bases (adenine, cytosine, guanine, thymine or uracil) and modified nucleotides that are modified at the sugar, phosphate, and/or base moiety.

"Identity" refers to sequence identity between two nucleic acid molecules. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.In the present invention, the identity of a sequence with SEQ ID NO: 1 is determined by calculating the number of bases (n) of the entire sequence (N bases with N≧15) which are identical with the bases of SEQ ID NO: 1. The percent identity (p) is 100 n/N.

"homologous" refers to a nucleic acid molecule having enough identity to another one to lead to RNAi activity, more particularly having at least 70% identity, preferably 80% identity and more preferably 90%.

"complementary" refers to the ability of a nucleic acid to form hydrogen bond(s) by either traditional Watson-Crick base-pairing or other non-traditional type base-pairing. In reference to the nucleic acid molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well-known in the art (see, e;g., Turner et al., 1987, *CSH Symp. Quant. Biol.*, 1987, LII, pp 123-133, Frier et al., *P.N.A.S.*, 1986, 83, 9373-9377; Turner at al., *J. Am. Chem. Soc.*, 1987, 109, 3783-3785). A percent complementarity indicates the percentage of contiguous residues in a nucleic acid molecule that can form hydrogen bonds (e.g., Watson-Crick base-pairing) with a second nucleic acid sequence (e.g., 5, 6, 7, 8, 9, or 10 nucleotides out of a total of 10 nucleotides, in the first oligonucleotide being base-paired to a second nucleic acid sequence having 10 nucleotides represents 50%, 60%, 70%, 80%, 90% and 100% complementarity, respectively). "Perfectly complementary" means that all the contiguous residues of a nucleic acid sequence will hydrogen bind with the same number of contiguous residues in a second nucleic acid sequence.

"target gene" refers to a gene whose expression is to be down-regulated.

"target sequence" refers to the portion of the mRNA which is complementary to the antisense region of the siNA molecule.

"vector" refers to a nucleic acid molecule capable of transporting another nucleic acid to which it has been linked.

"anticancer agent", "anticancer therapy" refers to both chemotherapy using cytotoxic agents and radiotherapy.

The short interfering nucleic acid (siNA) molecule according to the invention is specific to the Bcl-$X_L$ transcript (mRNA) and targets 19 contiguous nucleotides corresponding to positions 849 to 867, by reference to the human sequence NCBI accession number NM_138578 (SEQ ID NO: 2 in the attached sequence listing). The target of the siNA molecule according to the invention is included in the 189 nucleotides sequence at the 3' end of Exon 2 of the BCL2L1 gene (positions 742 to 930 of SEQ ID NO: 2). This target is absent in Bcl-$X_S$ transcript. Furthermore, the target is located in a region of the Bcl-$X_L$ transcript which is outside the regions of homology with the Bcl-2 transcript (positions 741 to 843 and 907 to 947 of SEQ ID NO: 2).

The siNA molecule according to the present invention inhibits specifically the Bcl-$X_L$ mRNA and protein expression. The siNA has no effect on the expression of the pro-apoptotic Bcl-$X_S$ protein or other Bcl-2 family members such as Bcl-2 and Mcl-1.

Inhibition of Bcl-$X_L$ expression may be assessed by any RNA or protein analysis technique, which is well-known in the art (Northern-blot, Western-blot, quantitative RT-PCR).

In addition the siNA molecule of the present invention has an antitumoral activity in vivo, that can be assayed in appropriate animal models known to those of ordinary skill in the art.

The invention encompasses the synthetic, semi-synthetic or recombinant siNA that inhibit the expression of the Bcl-$X_L$ mRNA and protein from any organism. SEQ ID NO: 1 is the human target sequence, i.e., the portion of the human mRNA which is complementary to the antisense region of the siNA molecule. Given the positions of the target in the human mRNA sequence, one skilled in the art will easily find the corresponding positions in the homologous sequences of other organisms (eukaryotes, for example mammals) which are accessible in the data bases such as the NCBI database (htt://www.ncbi.nlm.nih.gov/). Such homologous sequences can be identified as is known in the art, for example using sequence alignment. In addition, the siNA molecule of the invention may inhibit the expression of target gene variants, for example polymorphic variants resulting from haplotype polymorphism.

siNA molecules can be designed to target such homologous sequences, for example using perfectly complementary sequences or by incorporating non-canonical base pairs, for example mismatches and/or wobble base pairs, including flipped mismatches, single hydrogen bond mismatches, trans-type mismatches, triple base interactions and quadruple base interactions, that can provide additional target sequences. For example, the siNA molecule can be designed to target a sequence that is unique to a specific target gene mRNA sequence (a single allele or single nucleotide polymorphism (SNP)) due to the high degree of specificity that the siNA molecule requires, to mediate RNA activity. Alternatively, when mismatches are identified, non-canonical base-pairs (for example mismatches and/or wobble bases) can be used to generate siNA molecule that target more than one sequence. In a non-limiting example, non-canonical base-pairs such as uu and cc base pairs are used to generate siNA molecules that are capable of targeting homologous target mRNA sequences. In this approach, a single siNA can be used to inhibit expression of more than one mRNA instead of using more than one siNA molecule to target the different mRNAs.

In one embodiment, the invention features a siNA molecule wherein each strand comprises or consists of 15 to about 30 (e.g. about 15, 16, 17, 18, 19, 20, 21, 22, 23, 24, 25, 26, 27, 28, 29, or 30) nucleotides, and each strand comprises at least 15 to about 30 (e.g. about 15, 16, 17, 18, 19, 20, 21, 22, 23, 24, 25, 26, 27, 28, 29, or 30 nucleotides) nucleotides that are complementary to the nucleotides of the other strand. For example, the siNA molecule of the invention comprises or consists of a 19 to 21-nucleotide duplex (19 to 21 base pairs).

In another embodiment of the invention, the siNA molecule comprises or consists of ribonucleotide(s) (2'-OH nucleotides).

In another embodiment, the invention features a siNA molecule wherein the sense region comprises or consists of the sequence SEQ ID NO: 1 and the antisense region comprises or consists of the sequence SEQ ID NO: 4. This siNA targets the human gene (Table I).

TABLE I

| siNA targeting the human gene | | |
|---|---|---|
| | Sequence | Identification number |
| Sense strand | 5'-auuggugagucggaucgca-3' | SEQ ID NO: 1 |
| Antisense strand | 5'-ugcgauccgacucaccaau-3' | SEQ ID NO: 4 |

In another embodiment of the invention, the siNA molecule compnses overhanging nucleotide(s) at one or both end(s), preferably, 1 to about 3 (e.g. about 1, 2, or 3) overhanging nucleotides. The overhanging nucleotides which are advantageously at the 3' end of each strand, are preferably 2'-deoxynucleotide(s), preferably 2'deoxypyrimidine(s), such as a 2'-deoxythymidine(s). For example, the siNA molecule of the invention is a 21-nucleotide duplex, with 19 base pairs and 3'-terminal tt overhang(s). In particular, the sense strand is of the sequence SEQ ID NO: 5 and the antisense strand is of the sequence SEQ ID NO: 6; this siNA, noted siXL1, corresponds to SEQ ID NO: 1 (sense strand) and SEQ ID NO: 4 (antisense strand) with tt overhangs added at the 3' ends.

In another embodiment of the invention, the siNA molecule comprises blunt end(s), where both ends are blunt, or alternatively, where one of the ends is blunt. For example, the siNA molecule of the invention is a 19 to 21-nucleotide duplex, with 19 to 21 base pairs and blunt ends.

In another embodiment of the invention, the siNA molecule is assembled from two separate oligonucleotide fragments or strands, wherein one fragment (sense strand) comprises the sense region and the second fragment (antisense strand) comprises the antisense region of the siNA molecule.

In another embodiment, the invention features a siNA molecule wherein the sense region is connected to the antisense region via a linker molecule, such as a nucleotide or non-nucleotide linker. A nucleotide linker can be a linker of at least 2 nucleotides in length, for example about 3, 4, 5, 6, 7, 8, 9, or 10 nucleotides in length. Examples of such siNA molecules include small hairpin nucleic acid (shNA) molecules.

A non-nucleotide linker comprises abasic nucleotides, aptamers, polyether, polyamine, polyamide, peptide, carbohydrate, lipid, polyhydrocarbon, or other polymeric compounds.

In another embodiment of the invention, the siNA molecule comprises mismatches, bulges, loops or wobble base pairs to modulate the activity of the siNA molecule to mediate RNA interference.

In addition, the siNA molecule may include one or more modifications that increase resistance to nuclease degradation in vivo and/or improve cellular uptake. The siNA may include nucleotides that are modified at the sugar, phosphate, and/or base moiety, and/or modifications of the 5' or 3' end(s), or the internucleotidic linkage.

In another embodiment of the invention, the siNA molecule comprises one or more modified pyrimidine and/or purine nucleotides, preferably on each strand of the double-stranded siNA. More preferably, said modified nucleotides are selected from the group consisting of: 2'-O-methylnucleotides, 2'-O-methoxyethylnucleotides, deoxynucleotides, such as 2'-deoxynucleotides and 2'-deoxy-2'-fluoronucleotides, universal base nucleotides, acyclic nucleotides and 5-C-methyl nucleotides. A siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA molecule. The percent modification can be based upon the total number of nucleotides present in the sense strand, antisense strand or both the sense and the antisense strands.

In another embodiment, the invention features a siNA molecule wherein the strand comprising the sense region (sense strand) includes a terminal cap moiety at the 5'-end, the 3'-end, or both the 5' and 3' ends of the strand, preferably a deoxy abasic moiety or glyceryl moiety.

In another embodiment, the invention features a siNA molecule wherein the strand comprising said antisense region (antisense strand) includes a phosphate group at the 5'-end.

In another embodiment of the invention, the siNA molecule comprises at least one modified internucleotidic linkage, such as a phosphorothioate linkage.

The siNA molecules according to the invention may be produced by chemical synthesis by using well-known oligonucleotides synthesis methods which make use of common nucleic acid protecting and coupling groups, such as dimethoxytrityl at the 5'-end and phosphoramidites, at the 3' end. The nucleic acid molecules of the present invention can be modified to enhance stability by modification with nuclease resistant groups, for example 2'-amino, 2'-C-allyl, 2'-fluoro, 2'-O-methyl, 2'-H (for a review see Usman and Cedergren, *TIBS*, 1992, 17, 34 and Usman et al., *Nucleic Acids Symp. Ser.*, 1994, 31, 163). Examples of such modified oligonucleotides include with no limitation: 2' F-CTP, 2' F-UTP, 2' NH$_2$-CTP, 2' NH$_2$-UTP, 2' N$_3$-CTP, 2-thio CTP, 2-thio UTP, 4-thio UTP, 5-iodo CTP, 5-iodo UTP, 5-bromo UTP, 2-chloro ATP, Adenosine 5'-(1-thiotriphosphate), Cytidine 5'-(1-thiotriphosphate), Guanosine-5'-(1-thiotriphosphate), Uridine-5'-(1-thiotriphosphate), Pseudo-UTP, 5-(3-aminoallyl)-UTP and 5-(3-aminoallyl)-dUTP. siNA contructs can be purified by gel electrophoresis using general methods or can be purified by high pressure liquid chromatography (HPLC) and re-suspended in water.

The chemically-synthesized siNA molecule according to the invention may be assembled from two distinct oligonucleotides which are synthesized separately. Alternatively, both strands of the siNA molecule may be synthesized in tandem using a cleavable linker, for example a succinyl-based linker.

Alternatively, the siNA molecules of the invention may be expressed (in vitro or in vivo) from transcription units inserted into DNA or RNA vectors known to those skilled in the art and commercially available.

The invention relates also to a transcription unit comprising: a transcription initiation region, a transcription termination region, and a nucleic acid sequence encoding a least one siNA molecule according to the present invention, wherein said nucleic acid sequence is operatively linked to said initiation region in a manner that allows expression and/or delivery of the siNA molecule.

The nucleic acid sequence may encode one or both strands of the siNA molecule, or a single self-complementary strand that self-hybridizes into a siNA duplex.

The transcription initiation region may be from a promoter for a eukaryotic RNA polymerase I, II or III (pol I, II or III). Transcripts from pol II or pol II promoters are expressed at high levels in all cells. Alternatively, prokaryotic RNA polymerase promoters may be used, providing that prokaryotic RNA polymerase enzyme is expressed in the appropriate cells. Transcription units derived from genes encoding U6 small nuclear transfer RNA and adenovirus VA RNA are useful in generating high concentrations of desired siNA in cells.

The invention concerns also an expression vector comprising a nucleic acid encoding at least one siNA molecule of the instant invention. The expression vector may encode one or both strands of the siNA molecule, or a single self-complementary strand that self-hybridizes into a siNA duplex. The nucleic acid encoding the siNA molecule of the instant invention is preferably inserted in a transcription unit as defined above.

Large numbers of DNA or RNA vectors suitable for siNA molecule expression are known to those of skill in the art and commercially available. The recombinant vectors can be DNA plasmids or viral vectors. SiNA expressing viral vectors can be constructed based on, but not limited to, adeno-associated virus, retrovirus, adenovirus or alphavirus. The recombinant vectors capable of expressing the siNA molecules can be delivered in vivo, and persist in target cells. Alternatively, viral vectors can be used to provide transient expression of siNA molecules.

The invention concerns also eukaryotic or prokaryotic cells which are modified by a vector as defined above.

The invention concerns also a pharmaceutical composition comprising at least a siNA molecule or an expression vector, as defined above, in an acceptable carrier, such as a stabilizer, a buffer and the like.

A pharmaceutical composition or formulation refers to a form suitable for administration, e.g., systemic or local administration, into a cell or subject, including for example a human. Suitable forms, in part, depend upon the use or the route of entry, for example oral, inhalation, or by injection. These compositions or formulations are prepared according to any method known in the art for the manufacture of pharmaceutical compositions.

In one embodiment, the invention features a composition wherein the siNA molecule or vector is associated to a compound that allows the delivery of the siNA/vector into the cancer cells and/or endothelial cells. The compound may be a membrane peptide, transporter, lipid, cationic polymer, PEI. Preferably, the siNA and the compound are formulated in microspheres, nanoparticules or liposomes. Furthermore, the siNA molecule or vector may be associated with a compound that allows a specific targeting of the tumor and/or endothelial cells, such as a ligand of a cell-surface antigen or receptor, for example a peptide such as a RGD peptide, a sugar, a folate or an antibody specific for said antigen/receptor.

In another embodiment, the invention features a composition comprising a combination of at least two different siNA molecules.

In particular, the composition comprises a siNA molecule as defined above and an other siNA molecule having an antitumoral effect.

siNA molecules having an antitumoral effect include with no limitations siNA targeting the Mcl-1 transcript. The siNAs consisting of a sense strand of the sequence SEQ ID NO: 7, 19 or 20 and an antisense strand of the sequence SEQ ID NO: 8, 21, and 22, respectively, are examples of Mcl-1-specific siRNAs.

In another embodiment, the invention features a composition wherein the siNA molecule or vector is associated with at least one anticancer drug.

The invention also concerns a siNA molecule or a vector as defined above, as a medicament.

The invention concerns also the use of a siNA molecule or a vector as defined above, for the manufacture of a medicament for treating cancer.

The invention concerns further the use of a combination of a short interfering nucleic acid molecule specific to the Bcl-$X_L$ transcript as defined hereabove (siNA or an expression vector comprising said siNA) and of a short interfering nucleic acid molecule targeting the Mcl-1 transcript for the manufacture of a cytotoxic medicament for treating cancer.

The cancer may be of any type. Preferably, the cancer is a solid tumor, for example an ovarian, nasopharyngeal, breast, prostate or colon carcinoma, a glioma, a mesothelioma or a melanoma.

In one embodiment of said use, the siNA molecule or vector is associated with an anticancer drug.

The invention concerns also a product containing at least a siNA molecule or vector as defined above, and an anticancer drug, as a combined preparation for simultaneous, separate or sequential use in anticancer therapy.

The anticancer drugs which are used in combination with the siNA molecule or the vector according to the invention are those commonly used in chemotherapy, and include: cytotoxic agents, such as alkylating agents, antimitotic agents and antimetabolites, anti-angiogenic factors, tyrosine kinase inhibitors, and BH3-domain mimetics.

BH3 mimetics are compounds which have a function similar to Bak BH3 peptide and bind to the hydrophobic pocket of the anti-apoptotic proteins of the Bcl-2 family such as Bcl-2 and Bcl-$X_L$. BH3I-2' (3-iodo-5-chloro-N-[2-chloro-5-((4-chlorophenyl)sulphonyl)phenyl]-2-hydroxybenzamide), HA14-1 (Ethyl 2-amino-6bromo-4-(1-cyano-2-ethoxy-2ethoxy-2oxoethyl)-4H-chromene-3-carboxylate), YC137 (2-Methoxycarbonylamino-4-methylsulfanyl-butyric acid, 4-(4,9-dioxo-4,9-dihydronaphto[2,3-d]thiazol-2ylamino)-phenylester) and ABT737 are examples of BH3 mimetics.

Preferred anticancer drugs are cisplatin (cis-diaminedichoroplatinum, CDDP or DDP), carboplatin, doxorubicine, pemetrexed (Alimta®), paclitaxel (Taxol®) and BH3 mimetics.

The siNA molecule according to the present invention is generally used as an adjuvant therapy following the surgical resection of the tumor(s). In addition, the siNA molecule according to the invention may be used in combination with other conventional anticancer therapies including radiotherapy and immunotherapy.

A pharmaceutically effective dose is that dose required to prevent, inhibit the occurrence or treat (alleviate a symptom to some extent, preferably all the symptoms) of a disease or state. The pharmaceutically effective dose of the siNA depends upon the type of cancer, the composition used, the route of administration, the type of mammal being treated, the physical characteristics of the specific mammal under consideration, concurrent medication, and other factors, that those skilled in the medical arts will recognize. Generally, an amount between 1 µg/kg and 100 mg/kg, preferably between 5 µg/kg and 100 µg/kg, body weight/day of active ingredients is administered.

The siNA of the invention may be administered by a single or multiple route(s) chosen from: intratumoral, for example intracerebral (intrathecal, intraventricular), percutaneous, subcutaneous, intravenous, intramuscular, intraperitoneal, intrarachian, oral, sub-lingual, or inhalation.

When the siNA molecule or vector is used in combination with chemotherapy or radiotherapy, it is preferably administered prior to the anticancer agent, more preferably at least 48 hours prior to the anticancer agent.

BRIEF DESCRIPTION OF THE DRAWINGS

In addition to the preceding features, the invention further comprises other features which will emerge from the description which follows, which refers to examples illustrating the siNA molecules and their uses according to the invention, as well as to the appended drawings in which.

B. exposure to 20 µg/ml cisplatin. C20: exposure to 20 µg/ml cisplatin alone. siRNA control/C20: exposure to a combination of control siRNA with 20 µg/ml cisplatin. siXL1/C20: exposure to a combination of siXL1 with 20 µg/ml cisplatin

EXAMPLES

Figure 1:
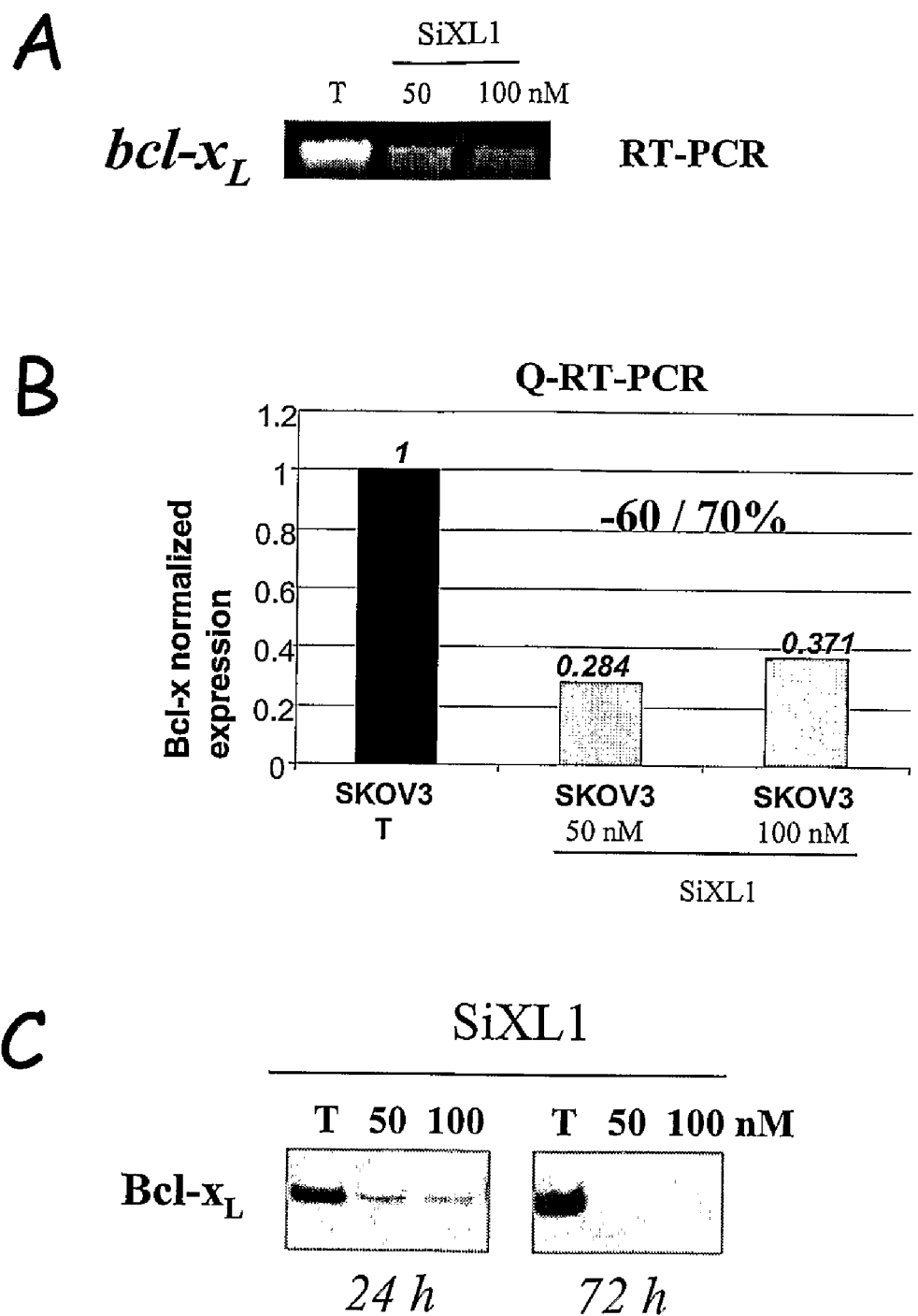
FIG. 1 illustrates the effect of siXL1 on Bcl-$X_L$ niRNA and protein expression in SKOV3 cells, 72 h after the transfection. [A]: RT-PCR; [B]: Quantitative RT-PCR and [C]: Western blot. T: untreated cells.

The following examples illustrate the invention but in no way limit it.

Example 1

Effect of siXL1 on Tumour Cells

1) Material and Methods
a) Cell Lines

SKOV3, OAW42, OAW42-R10, IGROV1 and IGROV1-R10 human ovarian adenocarcinoma cell lines, GL15 glioblastoma cell line, and NCI-H28 mesothelioma cell line were obtained from ECACC or ATCC. OAW42, OAW42-R10 cells were grown in DMEM (GIBCO-BRL) supplemented with 10% foetal calf serum (GIBCO-BRL), 2 mM Glutamax™ (GIBCO-BRL), 1 mM sodium pyruvate (GIBCO-BRL), 20 UI/L human recombinant insulin (LILLY), 33 mM sodium bicarbonate and 20 mM HEPES All the other cell lines were grown in RPMI 1640 medium (GIBCO-BRL) supplemented with 10% foetal calf serum (GIBCO-BRL), 2 mM Glutamax™ (GIBCO-BRL), 33 mM sodium bicarbonate and 20 mM HEPES. Cells were maintained at 37° C. in a 5% $CO_2$ humidified atmosphere, and split twice a week by trypsinization.
b) Chemicals Cisplatin (CDDP for cis-diamino-dichloro-platinum II) was obtained in the commercial form of Cisplatin from MERCK. Oligofectamine Reagent was obtained from INVITROGEN. It was supplied in liquid form and stored at 4° C. Linear polyethylenimine (L-PEI) was obtained from POLYPLUS-TRANSFECTION as an aqueous 100 mM solution in endotoxin-free water and stored at −80° C. prior to use.

c) In vitro Exposure to Cisplatin

Exponentially growing cells were exposed to CDDP for 2 hours at 37° C., in serum free medium. After exposure to the drug, the cell layers were rinsed and incubated in complete growth medium.

d) SiRNA Design and Transfection

Specific double-stranded 19-nucleotides RNA sequences homologous to the targeted mRNAs were used to silence Bcl-$X_L$ and Mcl-1 expression. The sequence of the double-stranded RNA used to block Bcl-$X_L$ expression, noted siXL1, is:

```
sense:
5'-auuggugagucggaucgcatt-3'   (SEQ ID NO: 5)

anti-sense:
5'-ugcgauccgacucaccaautt-3'   (SEQ ID NO: 6)
```

The sequence of the Mcl-1 specific siRNA is:

```
sense:
5'-gugccuuuguggcuaaacatt-3'   (SEQ ID NO: 7)

anti-sense:
5'-uguuuagccacaaaggcacct-3'   (SEQ ID NO: 8)
```

The sequence of the control siRNAs is:

```
sense:
5'-gacgugggacugaagggutt-3'    (SEQ ID NO: 9)

anti-sense:
5'-accccuucaguccacguctt-3'    (SEQ ID NO: 10)
```

The control siRNA does not bear any homology with any relevant human genes (Duxbury et al., 2003, precited). siXL1 targets selectively the Bcl-$X_L$ mRNA, but not the Bcl-$X_S$ mRNA. The siRNA Mcl-1 targets selectively the long isoform of Mcl-1 mRNA. SiRNAs were synthesized, HPLC purified and annealed by Eurogentec.

The siRNA duplexes were transfected according to the recommended procedure by using the Oligofectamine Reagent and Opti-MEM medium (INVITROGEN LIFE TECHNOLOGIES). 30-40% confluent cells were transfected in 25 cm² flasks with different concentrations of siXL1, siRNA Mcl-1 or siRNA control and incubated at 37° C., 5% $CO_2$ for 4 hours. Next, 20% fetal bovin serum was added to reach a final concentration of 10% foetal bovin serum in the 25 cm² flask.

e) RT-PCR

One µg of total RNA, extracted by RNAeasy kit (QIAGEN), was reverse-transcripted with 200 units Omniscript reverse transcriptase (QIAGEN) in first strand reaction conditions recommended by the manufacturer. The targeted cDNA were amplified using the following pair of primers, Bcl-$X_{L/S}$ forward 5'-ttggacaatggactggttga-3' (SEQ ID NO: 11) and Bcl-$X_{L/S}$ reverse 5'-gtagagtggatggtcagtg-3' (SEQ ID NO:12 ; Bargou et al., Int. J. Cancer, 1995, 16, 854-859), and amplified under the following cycling conditions: pre-incubation 94° C. for 5 min then 94° C. for 40 sec, 58° C. for 60 sec and 72° C. for 40 sec for 30 cycles, post-incubation 72° C. for 3 min within a Mastercycleur Gradient (EPPENDORF). The use of these primers allows the migration of Bcl-$X_s$ and Bcl-$X_L$ PCR products as two distinct bands of respectively 576 and 765 bp.

f) Real-time RT-PCR

One µg of total RNA, extracted by RNAeasy kit (QIAGEN), was reverse-transcripted with 200 units Omniscript reverse transcriptase (QIAGEN) in first strand reaction conditions recommended by the manufacturer. The Glyceraldehyde-3-phosphate deshydrogenase gene (GAPDH) was used to normalise Bcl-$X_L$ expression. The Bcl-$X_L$ and GAPDH cDNAs were amplified with the use of primers and Taqman-MGB probes which have been selected with the use of the Primer Express Applications-Based Primer Design Software (PERKIN-ELMER APPLIED BIOSYSTEMS).

For Bcl-$X_L$, following primers were used: 5'-tgcgtg-gaaagcgtagacaa-3' (SEQ ID NO:13) and 5'-aggtaagtggccatc-caagct-3' (SEQ ID NO:14), together with a Taqman-MGB probe presenting the following sequence: 5'-FAM-agatgcag-gtattggtg-TAMRA-3' (SEQ ID NO: 15).

For GAPDH, primers with the sequences 5'-gcaccgtcaag-gctgagaac-3' (SEQ ID NO: 16) and 5'-tctcgctcctggaagatggt-3' (SEQ ID NO: 17) were used together with a Taqman-MGB probe presenting the following sequence 5'-VIC-catcaatg-gaaatccca-TAMRA-3' (SEQ ID NO: 18). A Basic Local Alignment Search Tool (BLAST) search of the National Centre for Biotechnology Information (NCBI) database revealed no homology of the primer and probe sequences to any other known human genes. Data are presented relative to an untreated control sample chosen as calibrator.

Bcl-$X_L$ mRNA and GAPDH MRNA expression were measured separately by real time quantitative RT-PCR using Taq-Man technology (ABI PRISM 7000, PE APPLIED BIOSYSTEMS). For each PCR, a master mix was prepared with 2× reaction buffer (qPCR Mastermix, EUROGENTEC) containing dNTP, Hot Goldstar DNA polymerase, 5 mM $MgCl_2$, UNG and ROX. PCR was carried out with 400 nM of each primers for Bcl-$X_L$, 800 nM of each primers for GAPDH and 100 nM of appropriate probe. 5 µl of each diluted cDNA was added to 20 µl of the PCR master mix. Thermal cycling conditions comprised an initial UNG incubation at 50° C. for 2 min, Hot Goldstar DNA polymerase activation at 95° C. for 10 min, 50 cycles of denaturation at 95° C. for 15 sec, and annealing/extension at 60° C. for 1 min. Each run included the five points of the calibration curve for GAPDH and Bcl-$X_L$, the calibrator sample, the experimental samples, and a non-template control, all in triplicate.

Standard curves were established for Bcl-$X_L$ and GAPDH cDNA with five-fold serial dilution of Jurkat cell cDNA, which expresses Bcl-$X_L$. Threshold cycle (CT) was used to determine the quantity (Q) of Bcl-$X_L$ and GAPDH mRNA. Bcl-$X_L$ relative expression was calculated as follow: Bcl-$X_L$ expression=(Q Bcl-$X_L$/Q GAPDH)$_{sample}$/(Q Bcl-$X_L$/Q GAPDH)$_{calibrator}$. Results were analysed with SDS 2.0 software from APPLIED BIOSYSTEMS.

g) Western Blotting

Cells were rinsed with ice cold PBS and lysed in 150 mM NaCl, 50 mM Tris-HCl pH 8, 1% Triton X100, 4 mM PMSF, 2 mM Aprotinin, 5 mM EDTA, 10 mM NaF, 10 mM NaPPi, 1 mM $Na_3VO_4$ for 30 min on ice. Lysates were clarified by centrifugation at 10000 g for 10 min at 4° C. and protein concentrations were determined using the Bradford assay (BIO-RAD). Equal amounts of total cellular protein (20 µg) were resolved in a Bis-tris-HCL buffered (pH 6.4) 4-12% polyacrylamide gel (NuPAGE® Novex® 4-12% Bis-tris gel, INVITROGEN) for 35 min at 200V and electrophoretically transferred on a PVDF membrane (MILLIPORE) for 75 min at 30V. The membrane was blocked for 1 hour at room temperature in T-TBS (132 mM NaCl, 20 mM Tris-HCl pH 7.6, 0.05% Tween 20) supplemented with 5% non-fat dry milk. The membrane was incubated for 1 hour at room temperature in T-TBS-milk with the following primary antibodies: anti-Bcl-$X_{L/S}$ (1:500, S18 SANTA-CRUZ BIOTECHNOLOGY), anti-PARP (1:1000, CELL-SIGNALING TECHNOLOGY), anti-caspase-3 (1:1000, BD BIOSCIENCES PHARMINGEN) anti-cleaved caspase-3 (1:1000, CELL-SIGNALING TECHNOLOGY), anti-alpha-tubulin (1:3000, SIGMA) and anti-Mcl-1 (1:750, S19 SANTA-CRUZ BIOTECHNOLOGY). After three washes with T-TBS, the membrane was incubated for 1 h at room temperature in T-TBS-milk with the adequate peroxidase conjugated secondary antibody (Anti-rabbit IgG, CELL-SIGNALING TECHNOLOGY, and anti-mouse IgG, AMERSHAM). After 3 washes with T-TBS and one with TBS, the immunoreactivity was detected by enhanced chemiluminescence (ECL kit, AMERSHAM).

h) Morphological Characterization of Apoptotic Cells by Nuclear Staining with Diamidino-2-phenylindol (DAPI)

After treatment, detached cells were collected separately and adherent cells were dissociated by trypsin/EDTA. Adherent and detached cells were then pooled and centrifuged at 1500×g for 5 min before being fixed in 70% ethanol. The cells were then collected on a polylysine-coated glass slide by cytocentrifugation, before a 30 min room temperature incubation in a 1 µg/ml DAPI aqueous solution (BOEHRINGER MANNHEIM). Slides were thereafter extensively washed in distilled water and mounted in Mowiol (CALBIO-CHEM).

i) Flow Cytometry Analysis of DNA Cellular Content
Preparation of Cells.

After treatment, detached cells were collected separately. Adherent cells were then harvested by trypsin/EDTA dissociation. Adherent and detached cells were then pooled and washed in PBS before being fixed in 70% ethanol and stored at −20° C. until analysis. Before flow cytometry analysis, the cells were washed in PBS and incubated for 30 min at room temperature in PBS in order to allow the release of low molecular weight (m.w.) DNA, characteristic of apoptotic cells. After a centrifugation at 4000 g for 10 min, the cell pellets were resuspended and stained with propidium iodide (PI) using the DNA Prep Coulter Reagent Kit (BECKMAN-COULTER) at a final concentration of $10^6$ cells/ml.

Instrument Settings

Samples were analyzed using an EPICS XL flow cytometer (BECKMAN COULTER) equipped with an argon laser at 15 mW. PI-stained cells were analyzed using a 488 mn excitation. A 620 nm band pass filter was put on the red fluorescence of PI. Computerized gating was applied on the side and forward scatter to exclude very small debris and on pulse width and integral peak of red fluorescence to eliminate aggregates. All samples were analyzed at a flow rate lower than 100 events per second and with a sheath pressure of 30 psi.

Data Analysis:

EXPO 32 Acquisition Software (Beckman Coulter) was run for data acquisition.

2) Results a) siXL1 Effect on Bcl-$X_L$ Expression, Cell Growth Rate and Apoptosis Induction.

Figure 2:
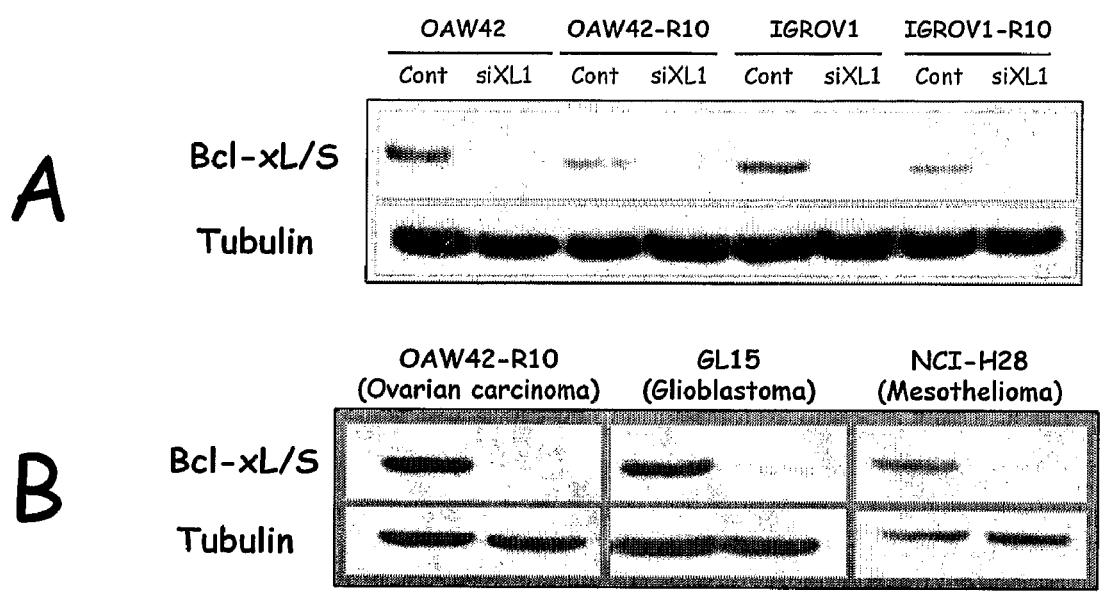
FIG. 2 illustrates the effect of siXL1 on Bcl-$X_L$ protein expression 72 h after the transfection, studied by Western blot in various ovarian carcinoma cell lines [A] and in tumour cell of various origins [B].
Figure 3:
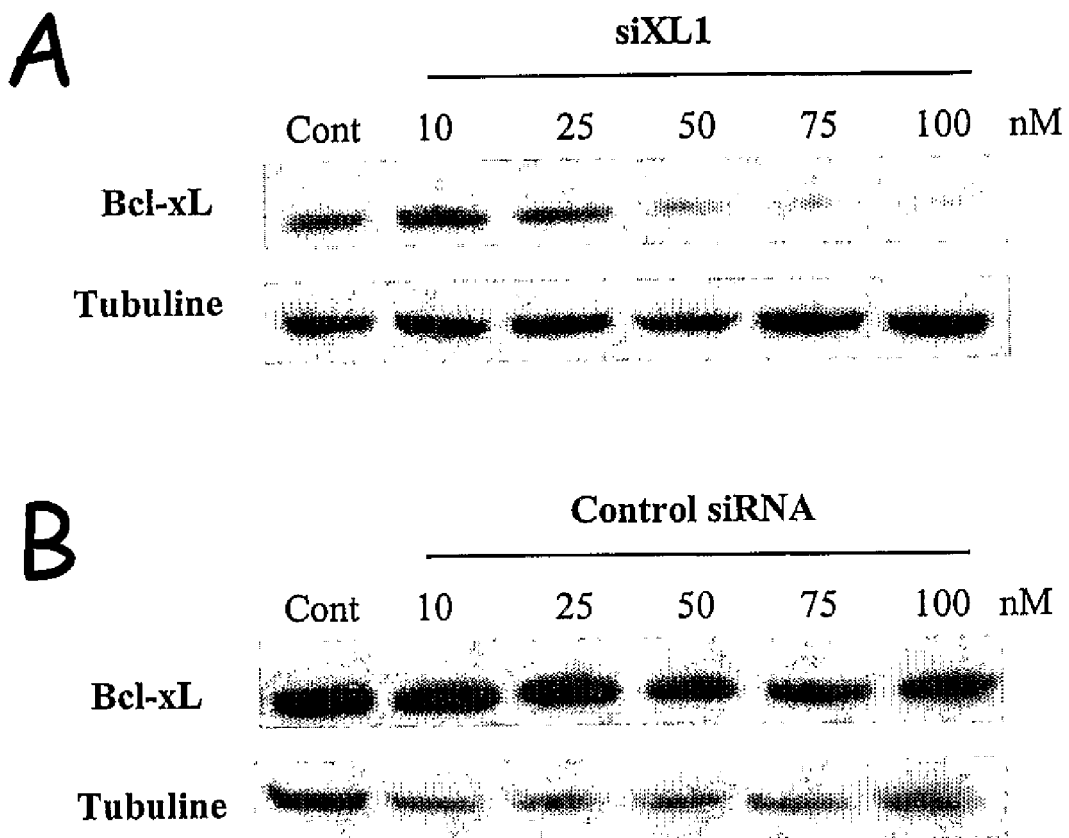
FIG. 3 illustrates the effect of various concentrations of siXL1 [A] or control siRNA [B] on Bcl-$X_L$ protein expression in SKOV3 cells, 72 h after the transfection.
Figure 4:
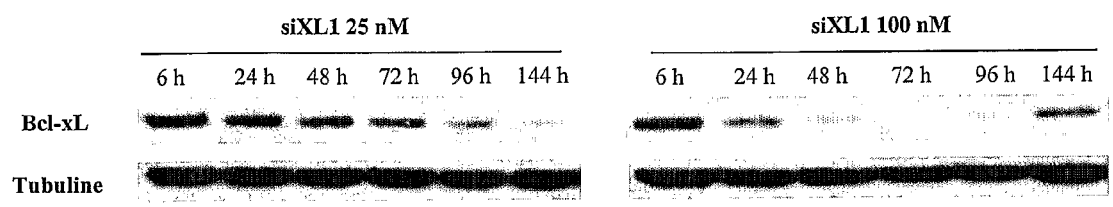
FIG. 4 illustrates the effect of 25 nM [A] or 100 nM [B] of siXL1 on Bcl-$X_L$ protein expression in SKOV3 cells, at various times after the transfection.
Figure 5:
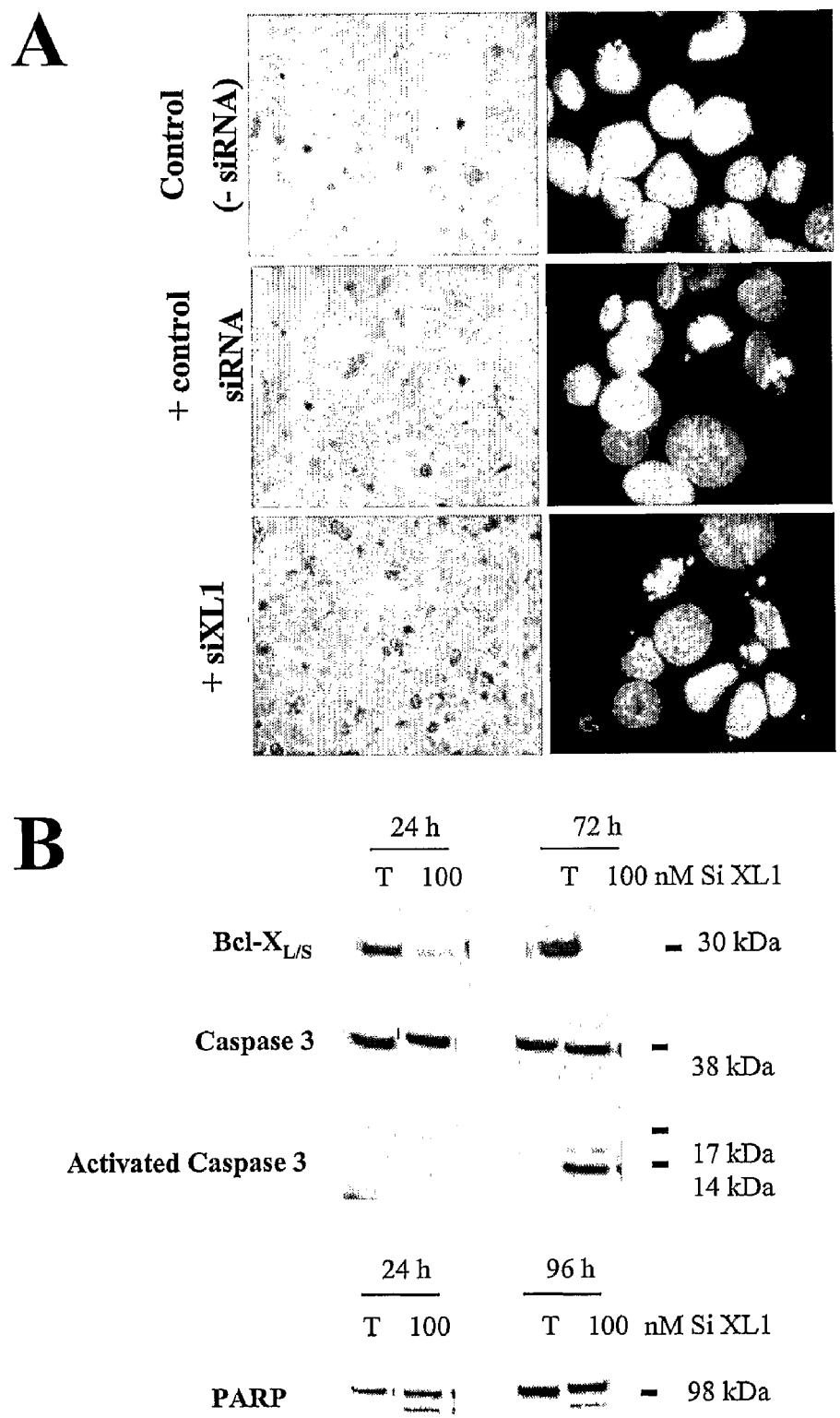
FIG. 5 illustrates apoptosis induction in SKOV3 cells by siXL1, 72 h after the transfection. A. Morphological observation of the cells (left panel) and the nuclei after DAPI staining (right panel) B. Caspase 3 activation and PARP cleavage are studied by Western blot. T: untreated cells.

The effects of siXL1, which targets selectively the Bcl-$X_L$ mRNA, but not the Bcl-$X_S$ mRNA, was tested in various tumour cell lines. SKOV3 cells treatment with siXL1 greatly reduces the Bcl-$X_L$ mRNA level, as demonstrated by RT-PCR analysis (FIG. 1A). Quantitative RT-PCR analysis revealed a 60% to 70% reduction of Bcl-$X_L$ mRNA level (FIG. 1B). Bcl-$X_L$ protein expression was reduced 24 hours after siXL1 transfection, and disappeared totally after 72 hours (FIG. 1C). The extinction of Bcl-$X_L$ protein expression was observed in various tumor cell lines tested: ovarian carcinoma cells, glioblastoma cells or mesothelioma cells (FIGS. 2A&B). The extinction of Bcl-$X_L$ protein expression by siXL1 is dose-dependent (FIG. 3A). No effect on Bcl-$X_L$ expression was detected in cells treated with the control siRNA (FIG. 3B). The kinetic of Bcl-$X_L$ protein expression extinction shows a maximum decrease after 72 hours of treatment with 100 nM siXL1 (FIG. 4), and a reappearance of Bcl-$X_L$ protein expression from 144 hours onwards. In cells treated with lower siXL1 dose (25 nM), the effect is greatly reduced and delayed (FIG. 4). siXL1 induces a moderate apoptosis in SKOV3 cells, as shown by cellular and nuclear morphology (FIG. 5A), and the detection of caspase 3 cleavage by Western blotting (FIG. 5B). The cleavage increases as much as Bcl-$X_L$ protein expression decreases.

b) Effect of siXL1/Cisplatin Combination on SKOV3 Cells in vitro.

Figure 6:
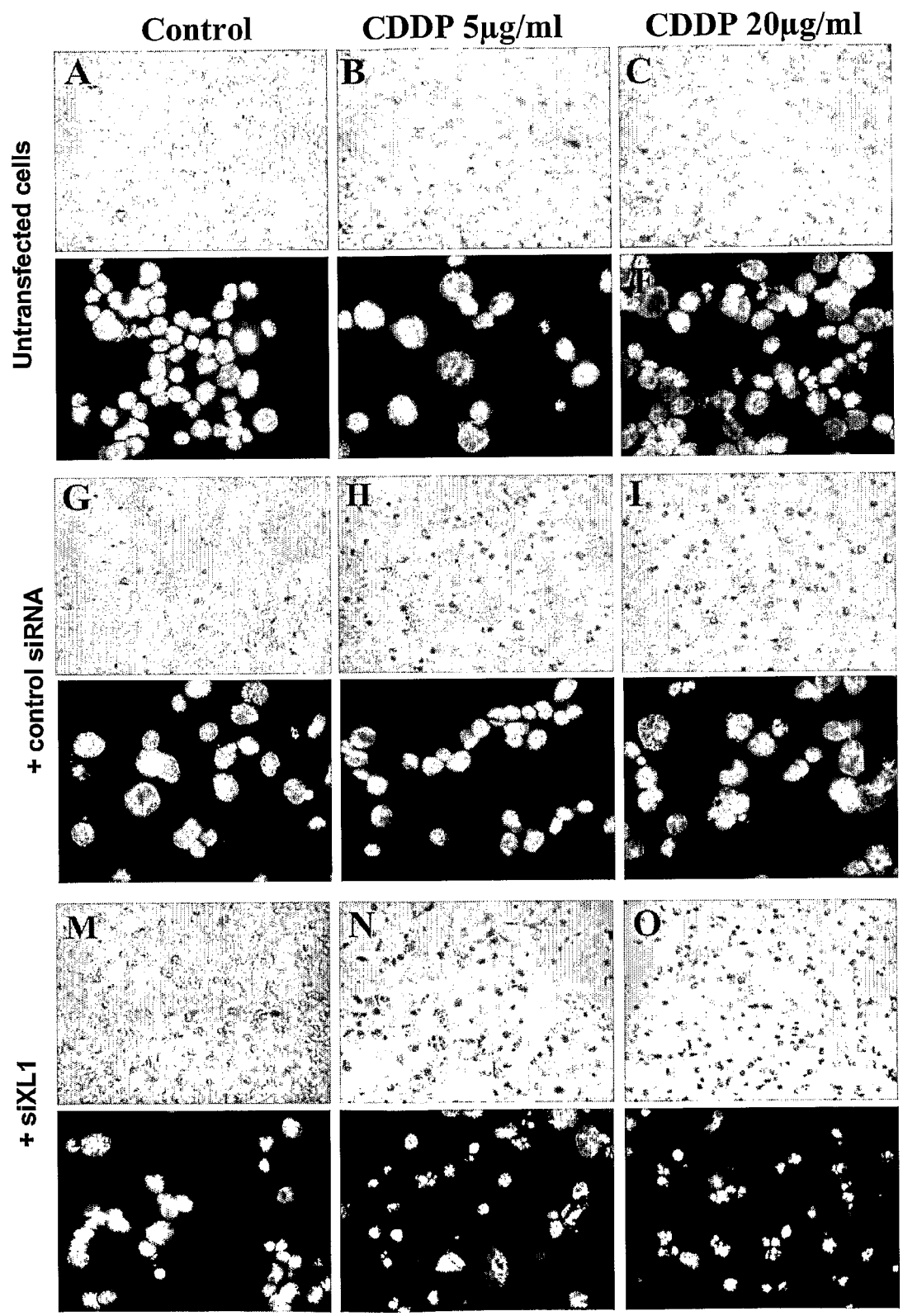
FIG. 6 illustrates the effect of the combination of siXL1 or control siRNA with cisplatin exposure on cell morphology and apoptosis induction, 144 h after the transfection, i.e. 96 h after the beginning of cisplatin exposure. Untransfected cells served as control. Cells transfected with siXL1 (M to R), control siRNA (G to L) or untransfected cells (A to E), were either not treated (control: A, D, G, J, M and P) or treated with either 5 µg/ml (B, E, H, K, N and R) or 20 µg/ml (C, F, I, L, O and R) cisplatin. Morphological observation of the cells: A, B, C, G, H, I, M, N, and O. Morphological observation of the cell nuclei after DAPI staining (D, E, F, J, K, L, P, Q and R).
Figure 7:
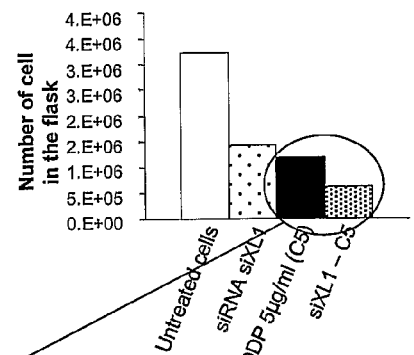
FIG. 7 illustrates the effect of the combination of siXL1 or control siRNA with cisplatin exposure on cell viability, 144 h after the transfection, i.e. 96 h after the beginning of cisplatin exposure. A. exposure to 5 µg/ml cisplatin. C5: exposure to 5 µg/ml cisplatin alone. siRNA control/C5: exposure to a combination of control siRNA with 5 µg/ml cisplatin. siXL1/C5: exposure to a combination of siXL1 with 5 µg/ml cisplatin.
Figure 7:
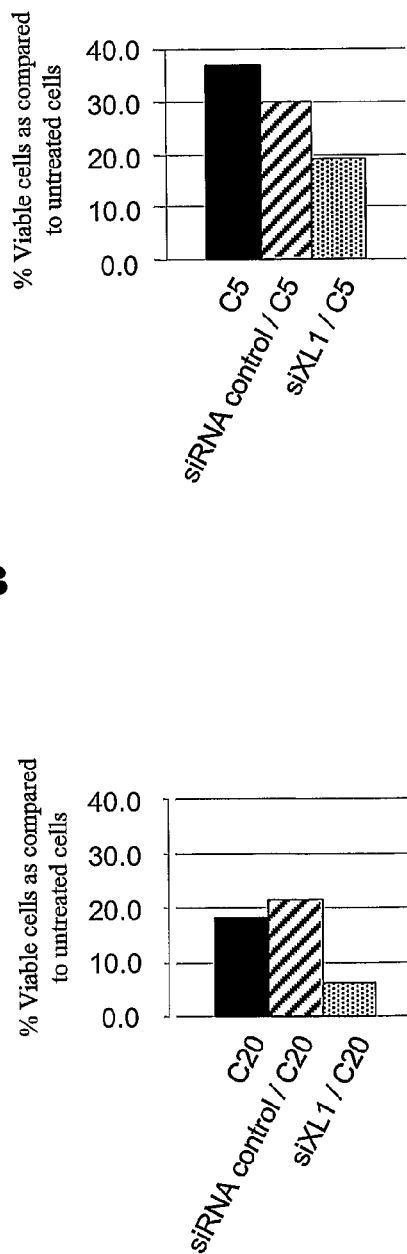
Figure 7:
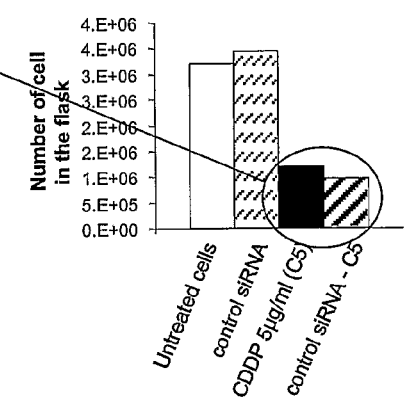
Figure 7:
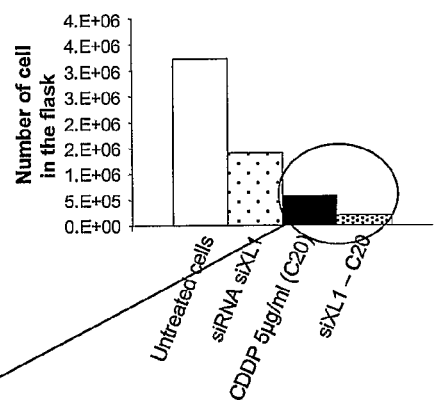
Figure 7:
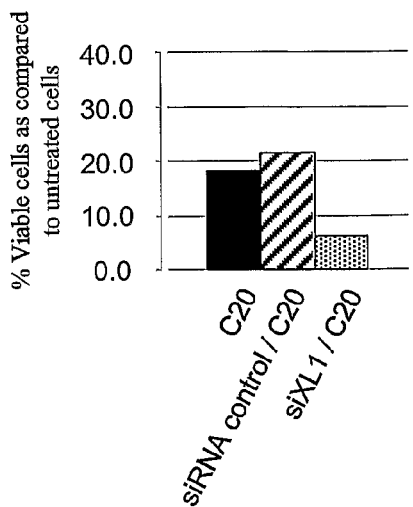
Figure 7:
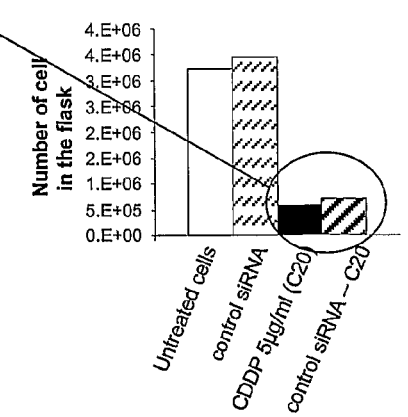
Figure 8:
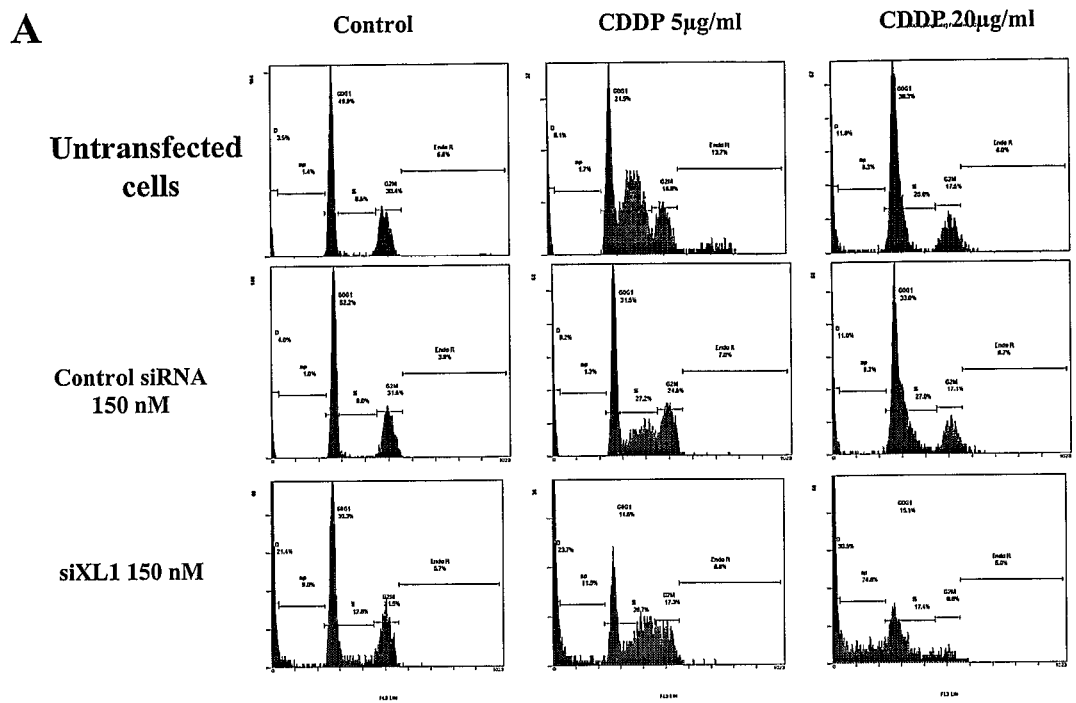
FIG. 8 illustrates the effect of the combination of siXL1 or control siRNA with cisplatin exposure on SKOV3 cell cycle. Untransfected cells served as control. Cells transfected with siXL1 (150 nM), control siRNA (150 nM) or untransfected cells, were either not treated (control) or treated with either 5 µg/ml or 20 µg/ml cisplatin (CDDP). Cell cycle was analysed 24 h (A) or 96 h (B) after the beginning of cisplatin exposure.
Figure 8:
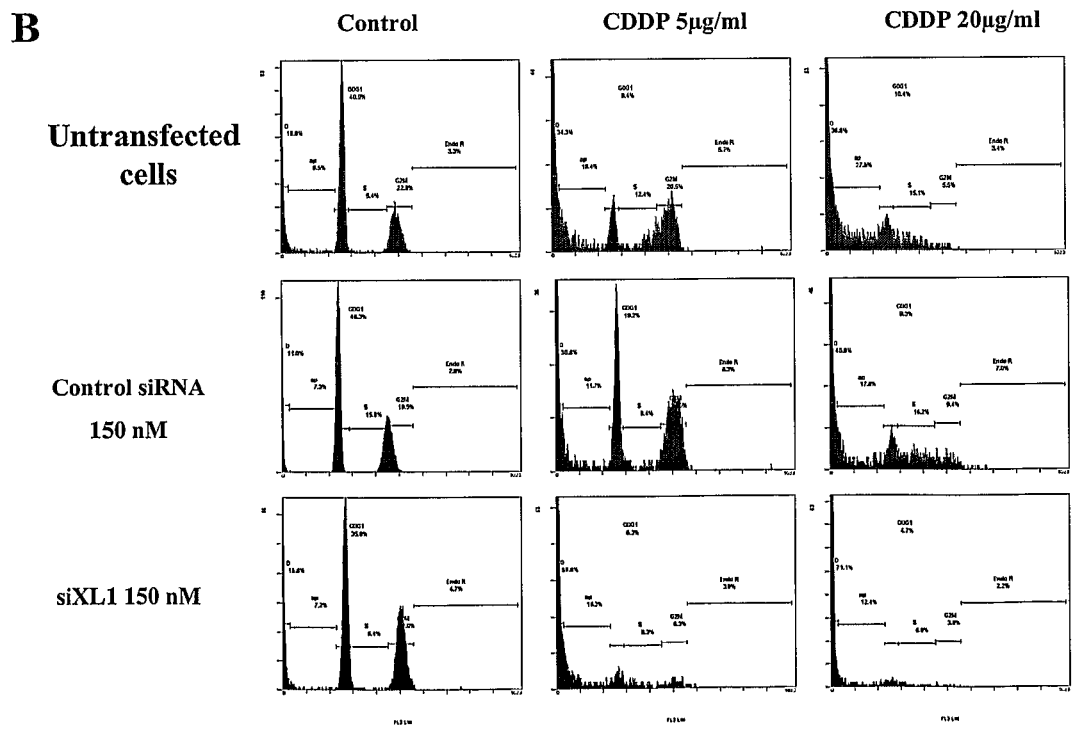

The exposure to the combination of cisplatin and siXL1 induces a high level of cell mortality after several days, in conditions where cisplatin alone induces only a transient arrest in cell cycle progression (5 and 20 µg/ml). A slight effect is detectable after 24 hours, whereas an abundant cell mortality is observed after 4 days of exposure to the combination of siXL1 with cisplatin; the viable cells representing less than 10% compared to the untreated cells (FIGS. 6, 7 and 8).

Figure 9:
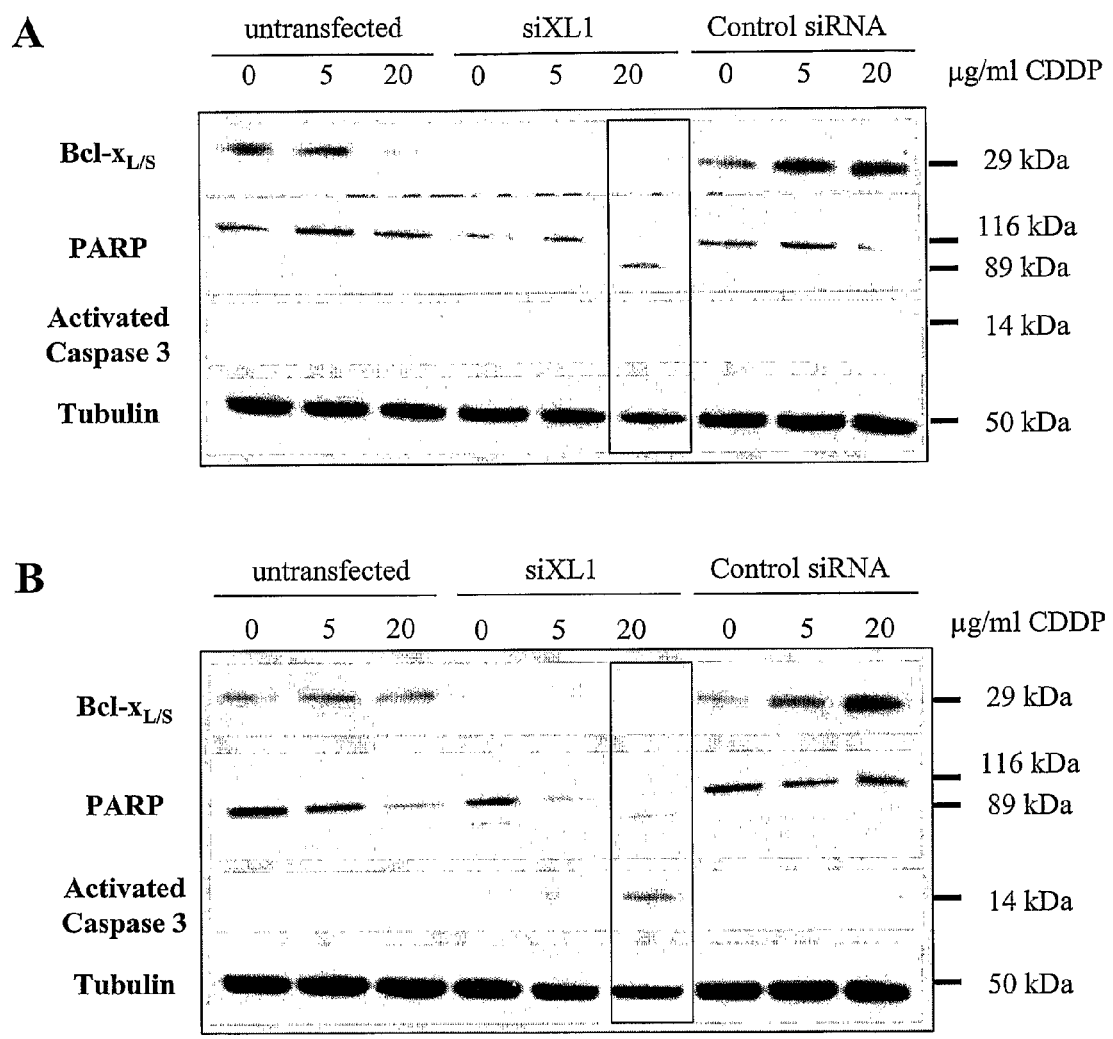
FIG. 9 illustrates the effect of the combination of siXL1 or control siRNA with cisplatin exposure on Bxl-xL expression and caspase 3 activation or PARP cleavage. Untransfected cells served as control. Cells transfected with siXL1 (150 nM), control siRNA (150 nM) or untransfected cells, were either not treated (0) or treated with either 5 µg/ml (5) or 20 µg/ml (20) cisplatin. Bxl-xL expression and caspase 3 activation or PARP cleavage was analysed 24 h (A) or 96 h (B) after the beginning of cisplatin exposure.

Gene expression analysis (FIG. 9) shows that cisplatin has no effect on Bcl-$X_L$ protein expression at the concentrations used (5 and 20 µg/ml), whereas with siXL1, Bcl-$X_L$ expression disappears almost completely 24 hours after exposure to cisplatin (72 hours after siRNA transfection). This modification of expression is transient, since Bcl-$X_L$ expression reappears 96 hours after cisplatin exposure (144 hours after transfection). Nevertheless, the expression is greatly repressed by the combination of siXL1 with the higher cisplatin dose (20 µg/ml), Bcl-$X_L$ protein expression being undetectable, even after the longest time.

The apoptosis induction, as demonstrated by caspase 3 activation and PARP cleavage detection, is greatly amplified by the combination of siXL1 with cisplatin. After 24 h exposure to cisplatin alone, no sign of apoptosis is detectable, whatever the concentration used. By contrast, in cells exposed to siXL1, caspase 3 and PARP cleavage is detectable, this cleavage is amplified in cells co-treated with 20 µg/ml cisplatin and siXL1. After 96 h exposure to cisplatin, the difference is clearly detectable, caspase 3 activation and PARP cleavage reaching their maximum when cisplatin is combined with siXL1.

Figure 10:
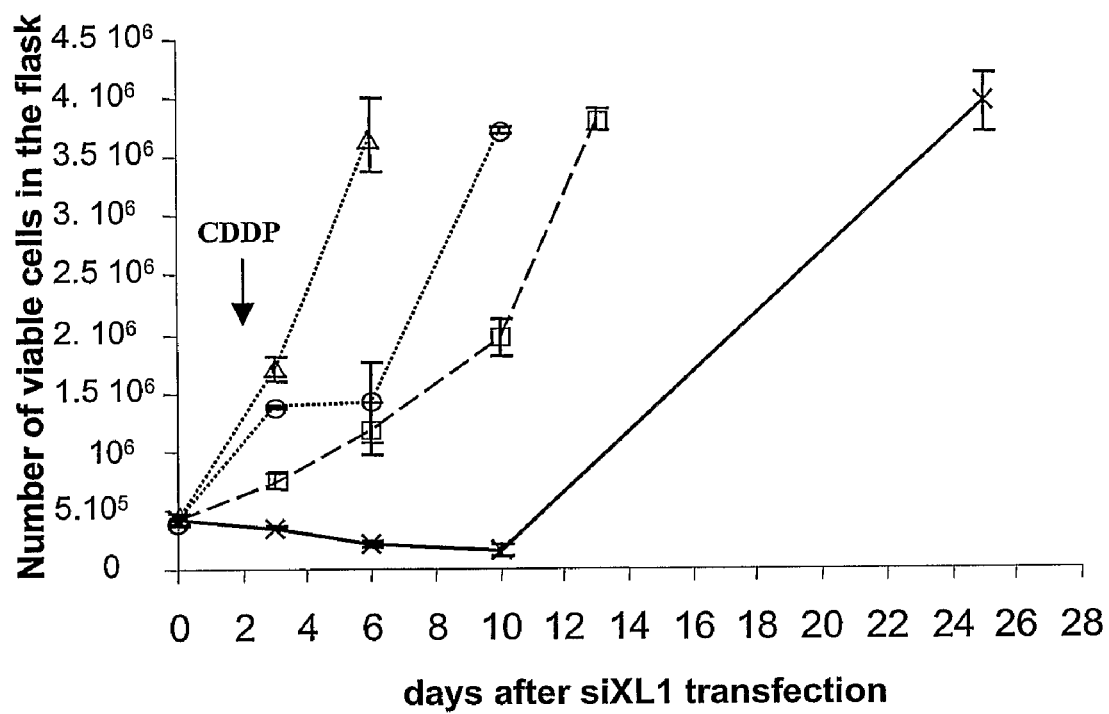
FIG. 10 illustrates SKOV3 cell growth after siXL1 transfection, combined or not to cisplatin exposure. 48 h after siXL1 transfection, the cells were treated for 2 h with 5 µg/ml CDDP (C5) or not treated, and cell viability was assessed by the trypan blue exclusion test at different times after treatment. Untransfected cells served as control. The result was expressed as a number of viable cells in 25 cm² flask and represent the mean of two independent countings. Δ: untransfected and untreated cells. ○: untransfected cells treated with 5 µg/ml CDDP alone. □: cells transfected with siXL1 and untreated. X: cells transfected with siXL1 and treated with 5 µg/ml CDDP.

These results confirm the morphological observations (FIGS. 6 and 7) and the FACS analysis of the cell cycle (FIG. 8), showing that cisplatin alone induces a low level or no cell death, whatever the concentration which is used (a cytostatic effect only is observed, due to a transient arrest in S and G2 phases), whereas siXL1 alone induces a moderate cell death by apoptosis. However, combination of siXL1 with cisplatin induces a massive cell death, that is dependent upon time, and to a lesser extent, to cisplatin dose. The cytotoxic effect of the siXL1/cisplatin combination is very strong even at the lowest cisplatin dose (5 µg/ml), and with 20 µg/ml, the destruction of the tumoral population is almost complete one week after the beginning of the treatment. The effect is specific, since the control siRNA induces no changes in the cisplatin effect. In addition, FIG. 10 shows that the association of siXL1 with a low cisplatin dose (5 µg/ml) induces a high mortality in SKOV3 cells and delayed strongly the tumor relapse in vitro.

These results show that the chosen siRNA sequence, siXL1, inhibits very efficiently Bcl-$X_L$ mRNA and protein expression and increases strongly the cytotoxic activity of cisplatin in an ovarian tumour cell line that is very aggressive and highly resistant to cisplatin. The siXL1 effect is specific, persists 96 hours and the optimal concentration of siXL1 is 150 nM.

c) siMcl-1 Effect on Mcl-1 Expression in SKOV3 Cells in vitro.

Figure 11:
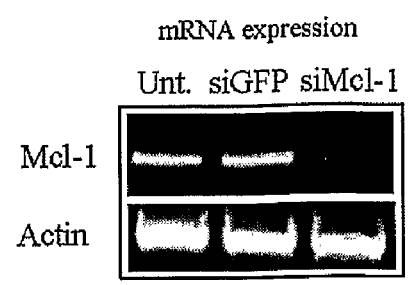
FIG. 11 illustrates the effect of siRNA-Mcl-1 (or siMcl-1) on Mcl-1 mRNA and protein expression in SKOV3 cells, 72 h after the transfection, by comparison with control siRNA (siGFP). [A]: RT-PCR ; [B]: Western blot. Unt.: untreated cells.
Figure 11:
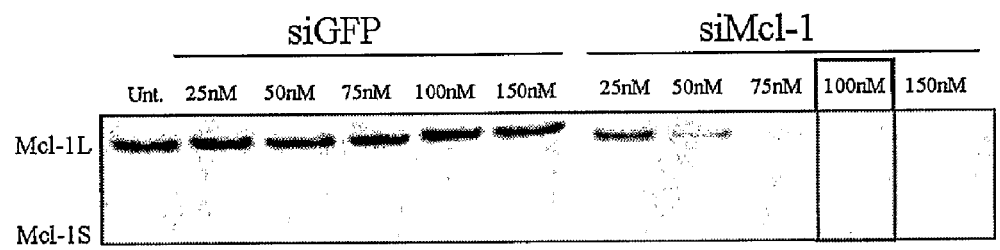

SKOV3 cells treatment with siMcl-1 reduces Mcl-1 mRNA expression almost completely, as demonstrated by RT-PCR analysis (FIG. 11A). Mcl-1 protein expression disappeared totally after 72 hours (FIG. 11B). The extinction of Mcl-1 protein expression by siXL1 is dose-dependent (FIG. 11B). No effect on Mcl-1 expression was detected in cells treated with the siGFP control siRNA (FIGS. 11A and 11B).

d) Effect of siXL1/siRNA Mcl-1 Combination on SKOV3 Cells in vitro.

Figure 12:
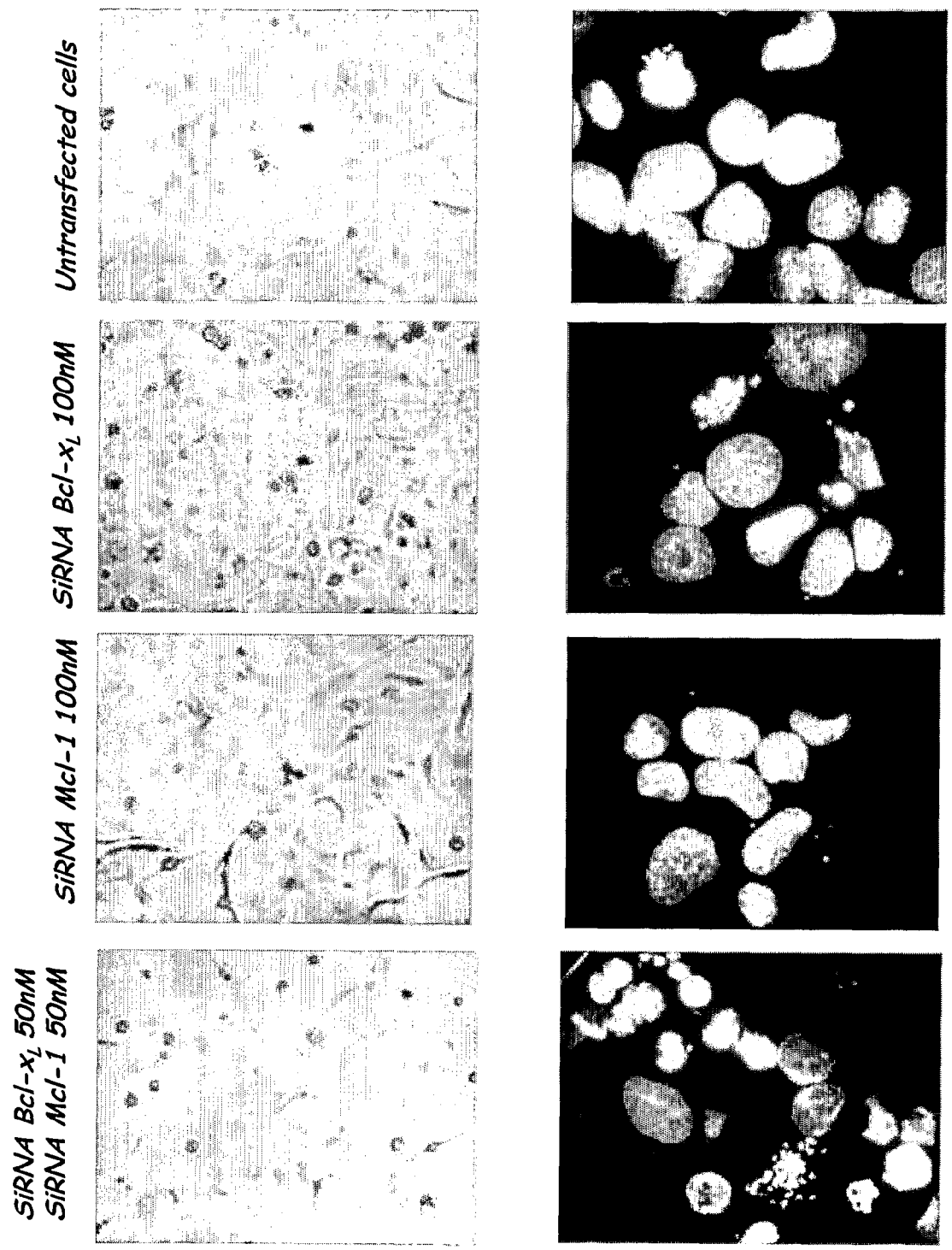
FIG. 12 illustrates the cytotoxic effect of the combination of siXL1 with a siRNA directed against Mcl-1 mRNA. Cells were transfected with siXL1 alone (100 nM), siRNA-Mcl-1 alone (100 nM) or a combination of siXL1 (50 nM) with siRNA-Mcl-1 (50 nM). Untransfected cells served as control. Morphological observation of the cells (Left panels). Morphological observation of the cell nuclei after DAPI staining (Right panels).

The exposure to the combination of siXL1 with a siRNA directed against the Mcl-1 mRNA produces a cytotoxic effect on SKOV3 cells (in the absence of cisplatin exposure) at concentrations where each siRNA produces no cytotoxic effect (50 nM; FIG. 12) or a slight cytoxic effect only (FIGS. 13 and 14).

Cellular and nuclear morphologies observation, as well as cell cycle analysis (FIG. 13) revealed no difference between untransfected SKOV3 cells and SKOV3 cells transfected with siMcl-1 or control siRNA, alone (150 nM each) or in combination (75 nM each). A slight reduction (20% to 40%) of the growth rate was observed.

Figure 13:
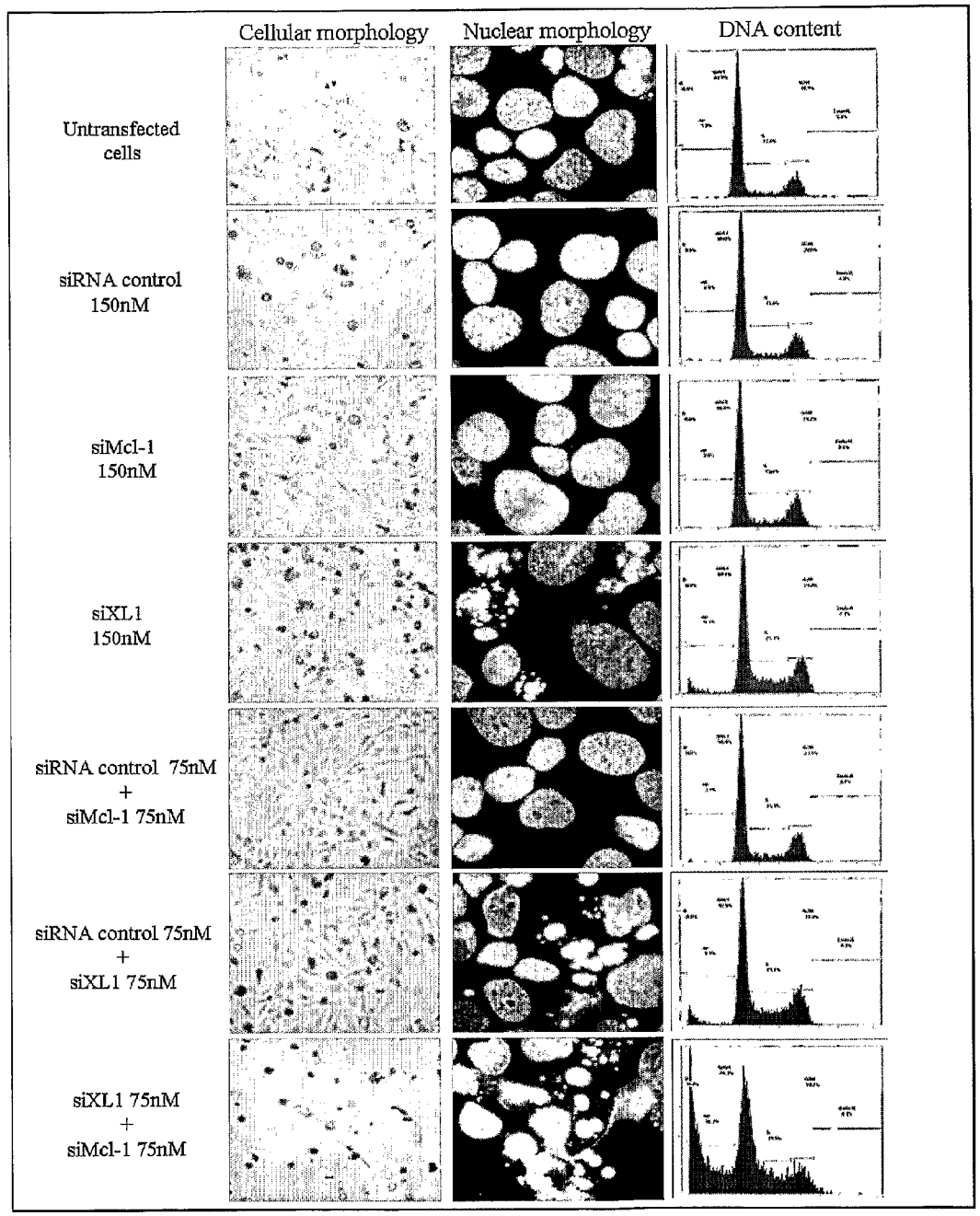
FIG. 13 illustrates the cytotoxic effect of the combination of siXL1 with a siRNA directed against Mcl-1 mRNA. Cells were transfected with siXL1, siRNA-Mcl-1 or siRNA control, alone (150 nM) or each (75 nM) in combination with one (75 nM) of the other two siRNAs. Untransfected cells served as control. Cellular response was analysed 72 h after cell transfection by cellular (left panel) and nuclear (middle panel) morphologies observation and FACs analysis of DNA content (right panel).
Figure 14:
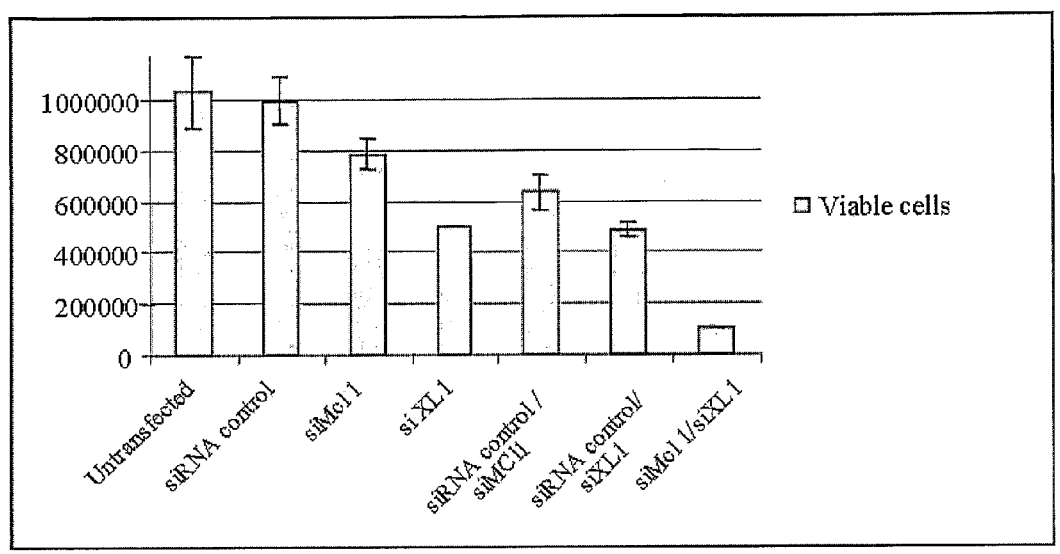
FIG. 14 illustrates the effects of the combination of siRNA targeting respectively $Bclx_L$ and Mcl-1 mRNA, onto SKOV3 cells viability. SKOV3 were transfected with siRNA control, siRNA targeting Mcl-1 mRNA (siMcl-1) and siRNA targeting $Bclx_L$ (siXL1), alone (150 nM) or each (75 nM) in combination with one (75 nM) of the other two siRNAs. Cellular viability was analysed by Trypan blue exclusion assay.

In the same conditions, SKOV3 cells transfected with siXL1 alone (150 nM each) or in combination with control siRNA (75 nM each) show a moderate apoptosis, as demonstrated by nuclear fragmentation and condensation, and a reduction of cell viability (FIGS. 13 and 14).

By comparison, the combination of siXL1 with siMc1 -1 (75 nM each) induces a massive cell detachment and cell death as demonstrated by the cell morphology, the presence of numerous nuclear features of cell death by apoptosis and of an important pre-G1 peak (FIGS. 13 and 14).

Example 2

Effect of siXL1 on Ovarian Tumors

1) Material and Methods
a) Nude Mice 4-week-old female Swiss/nude mice were obtained from CHARLES-RIVER LABORATORIES and maintained in a pathogen-free environment. The mice were fed a standard laboratory diet and tap water ad libitum and kept a 23±1° C. with a 12 h light/dark cycle. Animal experiments in the present study were performed in compliance with the guidelines of the Federation of european laboratory animal science associations.

b) PEI/siRNA Complex Formation and Administration

PEI/siRNA complexes were prepared in 5% glucose solution with a ratio of L-PEI nitrogen to siRNA phosphate of 5:1. Various amounts of siRNA (125, 625 or 2500 ng) and L-PEI were diluted separately, and PEI was then added to the siRNA. The solution was quickly homogenized and left for 15 min at room temperature. It was injected intraperitoneally in mice as a 0.5 ml 5% glucose solution.

c) Intraperitoneal Implantation of the Tumor Cells and siRNA Injection in Mice 6-8 weeks old mice were implanted intraperitoneally with $2 \times 10^7$ ovarian adenocarcinoma SKOV3 cells. As described previously, this model reflects the i.p growth pattern of advanced ovarian cancer (Louis et al, Cancer Gene Therapy, 2006, 13, 367-374).

$c_1$) Analysis of Mice Survival

Twenty one days after tumour implantation, mice were allocated to one of the eight treatment groups (10 mice per group) summarized in Table II:

Group 1 comprised untreated animals.
Group 2 received intraperitoneal injection of 4 µg/kg cisplatin in 1 ml 0.9% NaCl solution.
Group 3 received intraperitoneal injection of 25 µg/kg control siRNA in 1 ml 0.9% NaCl.
Group 4 received intraperitoneal injection of 25 µg/kg Bcl-$X_L$ siRNA in 1 ml 0.9% NaCl.
Group 5 received intraperitoneal injection of 25 µg/kg control siRNA in 1 ml 0.9% NaCl and the following day 4 µg/kg of cisplatin in 1 ml 0.9% NaCl solution.
Group 6 received intraperitoneal injection of 4 µg/kg of cisplatin in 1 ml 0.9% NaCl solution and the following day 25 µg/kg control siRNA in 1 ml 0.9% NaCl.
Group 7 received intraperitoneal injection of 25 µg/kg Bcl-$X_L$ siRNA in 1 ml 0.9% NaCl and the following day 4 µg/kg of cisplatin in 1 ml 0.9% NaCl solution.
Group 8 received intraperitoneal injection of 4 µg/kg of cisplatin in 1 ml 0.9% NaCl solution and the following day 25 µg/kg Bcl-$X_L$ siRNA in 1 ml 0.9% NaCl.

The same treatment was repeated one month later. Mice were killed and autopsied when considered as moribund. Organs and tumours were formalin-fixed and paraffin-embedded for histological examination. At the end of the experiment, all surviving animals were sacrificed, and histological examination was performed in order to detect residual tumour nodes.

TABLE II

| Treatment protocol | |
|---|---|
| Group | Treatment |
| 1 | Untreated |
| 2 | 4 µg/kg of cisplatin |
| 3 | 25 µg/kg control siRNA |
| 4 | 25 µg/kg Bcl-$X_L$ siRNA |
| 5 | 25 µg/kg control siRNA + 4 µg/kg cisplatin |
| 6 | 4 µg/kg cisplatin + 25 µg/kg control siRNA |
| 7 | 25 µg/kg Bcl-$X_L$ siRNA + 4 µg/kg cisplatin |
| 8 | 4 µg/kg cisplatin + 25 µg/kg Bcl-$X_L$ siRNA |

$c_1$) Effect of siRNA Delivery on Bcl-$X_L$ Expression in SKOV3 Tumour Nodes

After peritoneal carcinomatosis development, animals were injected intraperitoneally with 5, 25 or 100 µg/kg siXL1, naked or complexed with PEI. Mice were killed 3 days after transfection and each organ (kidney, liver, spleen, pancreas, ovary, peritoneum, diaphragm, lung, heart and skeletal muscle) was washed with saline solution. Parts of each organs were either frozen in liquid nitrogen and stored at –80° C. for RT-PCR and western blot analysis, or formalin-fixed and paraffin-embedded for histological examination and immunohistochemical analysis.

d) Subcutaneous Implantation of the Tumor Cells and siRNA Injection in Mice

SKOV3 cells ($2 \times 10^7$/500 µL) were inoculated subcutaneously into the right flank of nude mice, and establishment of palpable tumours was determined. The tumour volume was calculated as $v = L \times l^2 \times p/6$ where L and l represent the larger and the smaller tumour diameter measured twice week with digital caliper. When tumours reached an average volume of ~100 mm³ (on day 10), three experimental groups (three mice per group) were tested as follow: (a) untreated, (b) siXL1 naked (25 µg/kg), and (c) siXL1-PEI (25 µg/kg). The samples were diluted in 0.5 ml 0.9% NaCl solution (siRNA naked) or in 0.5 ml 5% glucose solution (siRNA-PEI) and injected intraperitoneally. This process was repeated once a week.

e) Immunohistochemistry

Immunohistochemical staining was performed on paraffin-embedded material. To perform immunostaining, 4 μm-thick sections were dewaxed, rehydrated and treated 30 minutes by high-temperature-heating antigen retrieval technique in citrate buffer 0.1M pH6 to unmask epitopes. Sections were incubated 1 hour at room temperature with polyclonal antibody anti-Bcl-$X_{L/S}$ (S18) obtained from Santa Cruz (TEBU-BIO) and diluted 1:50. After washes, slides were incubated with Rabbit IgG Vectastain ABC Kit (VECTOR, ABCYS) according to the manufacturer instructions. Staining was revealed with DAB chromogen system (DAKO) and sections were counterstained with hematoxylin.

2) Results

The effect of siXL1 in vivo was tested in a mouse model of human ovarian cancer. In this model, a peritoneal human ovarian adenocarcinoma is induced by intraperitoneal injection of SKOV3 human ovarian tumor cells, into nude mice.

a) Naked siRNA Injection

Figure 15:
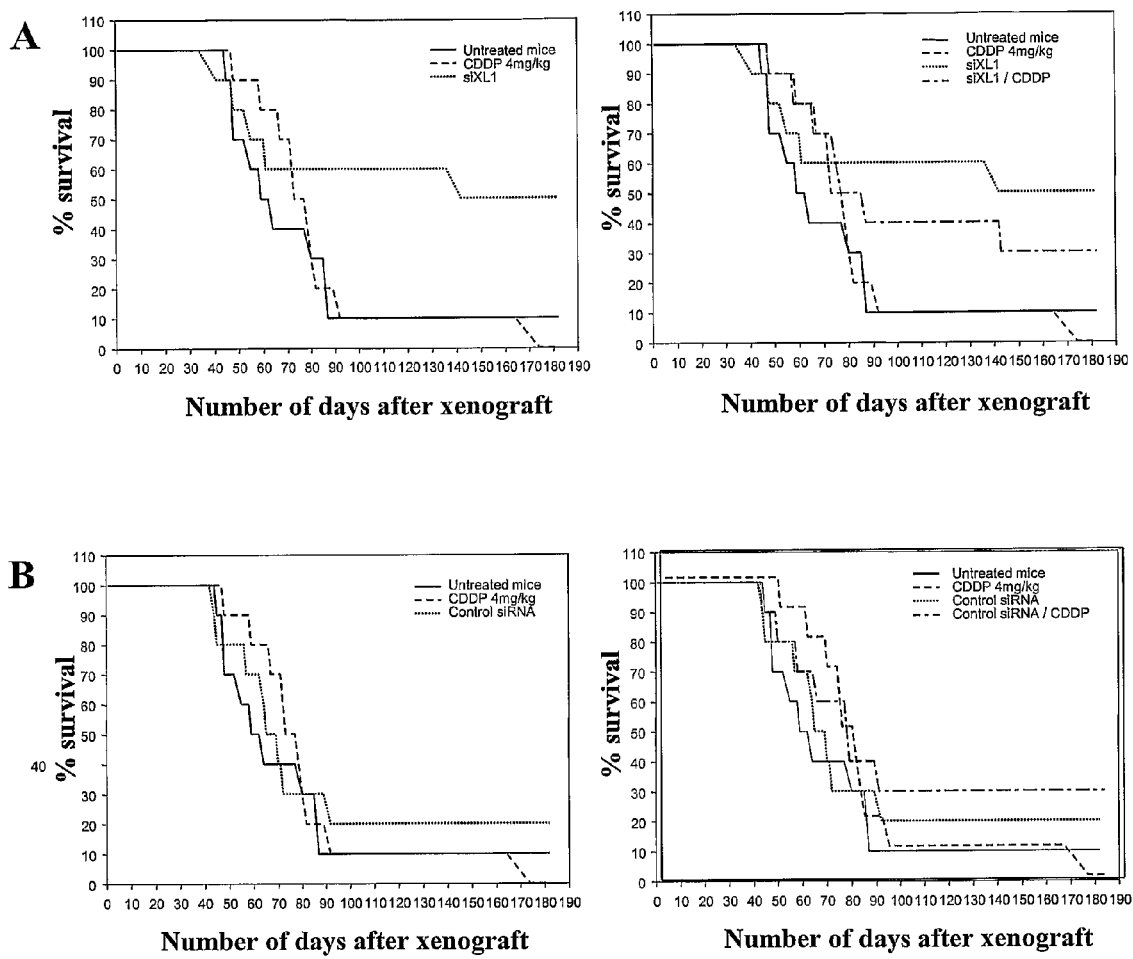
FIG. 15 illustrates intraperitoneal SKOV3 tumour bearing-mice's survival after treatment or not with siXL1 or control siRNA combined or not with cisplatin. A. Treatment with siXL1: mice were either untreated (left and right panel), treated with CDDP alone (4 mg/kg) (left and right panel), siXL1 alone (left and right panel), or a combination of siXL1 and CDDP (right panel) and the percentage of mice surviving was determined over a period of 190 days after the treatment. B. Treatment with control siRNA: mice were either untreated (left and right panel), treated with CDDP alone (4 mg/kg) (left and right panel), control siRNA alone (left and right panel), or a combination of control siRNA and CDDP (right panel) and the percentage of mice surviving was determined over a period of 190 days after the treatment.

The results show that siXL1 increases considerably the mice survival (60% survival at 130 days in the group treated with siXL1 versus 10% in untreated mice), whereas cisplatin treatment does not improve survival (FIG. 15). However, as opposed to the results observed in vitro, the combination of siXL1 with cisplatin produces an effect in vivo which is similar to that of siXL1 alone; the combination of siXL1 with cisplatin does not improve mice survival by comparison to siXL1 alone. It is worth noting that the dose of siRNA and the number of injections (2 injections at 28 days interval) are very low compared to those used in other studies (high dose siRNA every day or several times per week). This effect is specific, since the control siRNA does not increase the mice survival.

In the group treated with siXL1, the mice either die in the same interval as the control mice (50% of mice) or are cured, as demonstrated by the autopsy of mice after 150 days, showing no residual tumors in 50% of mice. The first half of the curves is identical in the different groups, indicating that the siRNA effect could be restricted to the smallest tumor nodules, maybe due to a direct effect of siXL1 on endothelial cells of the blood vessels. By contrast, mice having larger tumors at the time of the siXL1 injection are less sensitive to siXL1 treatment in these conditions (naked siRNA administration) and their survival rate is similar to that of the untreated group. An heterogeneity in tumor development between mice, in this model could thus explained these results since there is one month delay between the death of the first and the last mouse in the untreated group.

Molecular effect of siRNA on its target was shown by the immunohistochemical analysis of Bcl-$X_L$ protein in SKOV3 peritoneal tumour nodes. Untreated mice tumours show high Bcl-$X_L$ expression, despite a relative intra and inter individual variability. Mice treated with various amounts of naked siXL1 (5, 25 or 100 μg/ml), reveal a relative intra and inter individual variability with some nodes showing a high Bcl-$X_L$ expression level while other nodes show a reduced Bcl-$X_L$ expression level. Nevertheless, the labelling intensity decreases as the siXL1 dose increases, suggesting a dose effect of the siRNA.

b) siRNA/PEI Complexes Injection

Immunohistochemical analysis of Bcl-$X_L$ protein in SKOV3 peritoneal tumour nodes, in mice treated with siXL1, naked or complexed with L-PEI, shows that the overall Bcl-$X_L$ protein expression level is lower in mice treated with siXL1/L-PEI complexes, compared to mice treated with naked siXL1. These results indicate that siXL1 delivery by a vector (L-PEI: linear polyethylenimine) could increase its activity in vivo.

Figure 16:
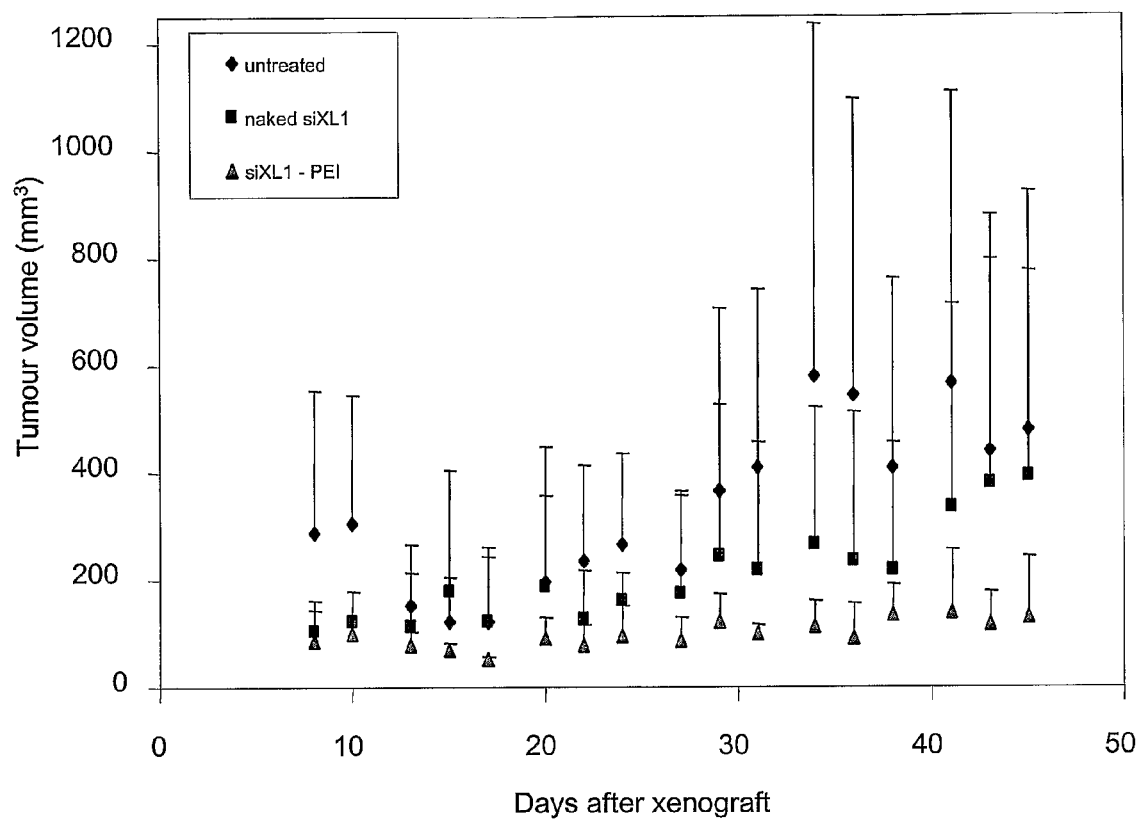
FIG. 16 illustrates the effect of siXL1, either naked or delivered by L-PEI, on tumour growth. $20 \times 10^6$ SKOV3 human ovarian carcinoma cells were implanted subcutaneously into nude mice and tumors were allowed to grow until they reached a size of ~10×10 mm (after 8 days). siXL1 complexed (▲) or not (■) with L-PEI were weekly injected intraperitoneally into SKOV3 tumour-bearing mice and the tumour volume was measured at different time after tumor implantation.

This was confirmed by the subcutaneous tumor growth analysis, showing that siXL1 delivered with PEI and injected intraperitoneally, inhibits tumor growth for at least 45 days, whereas naked siXL1 injected in the same conditions has almost no effect, as tumor growth is almost similar to that of the untreated mice (FIG. 16).

The invention claimed is:

1. A pharmaceutical composition comprising, in an acceptable carrier, at least:
   a double-stranded short interfering nucleic acid molecule specific to the Bcl-X$_L$ transcript comprising a sense and an antisense region, wherein the sense region comprises the nucleotide sequence SEQ ID NO: 1 or a sequence having at least 70% identity with said sequence, and the antisense region comprises a nucleotide sequence that is complementary to the sense region, and wherein each strand comprises 15 to about 30 nucleotides, and each strand comprises 15 to about 30 nucleotides that are complementary to the nucleotides of the other strand, and
   a short interfering nucleic acid molecule targeting the Mcl-1 transcript consisting of a sense strand of the sequence SEQ ID NO: 7 and an antisense strand of the sequence SEQ ID NO: 8.

2. The pharmaceutical composition according to claim 1, wherein said double-stranded short interfering nucleic acid molecule comprises a 19 to 21-nucleotide duplex.

3. The pharmaceutical composition according to claim 1, wherein said double-stranded short interfering nucleic acid molecule according to claim 1 comprises ribonucleotides.

4. The pharmaceutical composition according to claim 1, wherein the sense region of said double-stranded short interfering nucleic acid molecule specific to the Bcl-X$_L$ transcript comprises the nucleotide sequence SEQ ID NO: 1 and the antisense region of said double-stranded short interfering nucleic acid molecule specific to the Bcl-X$_L$ transcript comprises the nucleotide sequence SEQ ID NO: 4.

5. The pharmaceutical composition according to claim 1, wherein said double-stranded short interfering nucleic acid molecule comprises 1 to about 3 overhanging nucleotides at the 3' end of each strand.

6. The pharmaceutical composition according to claim 5, wherein said double-stranded short interfering nucleic acid molecule specific to the BcL-X$_L$ transcript consists of a sense strand of the sequence SEQ ID NO: 5 and an antisense strand of the sequence SEQ ID NO: 6.

7. The pharmaceutical composition according to claim 1, wherein said double-stranded short interfering nucleic acid molecule comprises blunt end(s).

8. The pharmaceutical composition according to claim 1, wherein said double-stranded short interfering nucleic acid molecule is assembled from two separate oligonucleotide fragments, wherein one fragment comprises the sense region and the second fragment comprises the antisense region of the short interfering nucleic acid molecule.

9. The pharmaceutical composition according to claim 1, wherein the sense region of said double-stranded short interfering nucleic acid molecule is connected to the antisense region via a linker molecule.

10. The pharmaceutical composition according to claim 1, wherein said double-stranded short interfering nucleic acid molecule comprises one or more modified pyrimidine and/or purine nucleotides.

11. The pharmaceutical composition according to claim 1, wherein the strand of said double-stranded short interfering nucleic acid molecule comprising the sense region includes a terminal cap moiety at the 5' and/or 3'-end(s).

12. The pharmaceutical composition according to claim 1, wherein the strand of said double-stranded short interfering nucleic acid molecule comprising said antisense region includes a phosphate group at the 5'-end.

13. The pharmaceutical composition according to claim 1, wherein said double-stranded short interfering nucleic acid molecule comprises at least one modified internucleotidic linkage.

14. The pharmaceutical composition according to claim 1, wherein it further comprises at least one anticancer drug.

15. The pharmaceutical composition according to claim 14, wherein the anticancer drug is selected from the group consisting of: cytotoxic agents, anti-angiogenic factors, tyrosine kinase inhibitors and BH3 mimetics.

16. The pharmaceutical composition according to claim 1, wherein said sense region of the short interfering nucleic acid molecule specific to the Bcl-X$_L$ transcript has at least 80% identity with SEQ ID NO: 1.

17. The pharmaceutical composition according to claim 1, wherein said sense region of the short interfering nucleic acid molecule specific to the Bcl-X$_L$ transcript has at least 90% identity with SEQ ID NO: 1.

18. The pharmaceutical composition according to claim 14, wherein the anticancer drug is a cytotoxic agent.

19. The pharmaceutical composition according to claim 1, wherein said short interfering nucleic acid molecule targeting the Mcl-1 transcript is assembled from two separate oligonucleotide fragments.

20. The pharmaceutical composition according to claim 1, wherein the sense strand of said short interfering nucleic acid molecule targeting the Mcl-1 transcript is connected to the antisense strand via a linker molecule.

21. The pharmaceutical composition according to claim 1, wherein said short interfering nucleic acid molecule targeting the Mcl-1 transcript comprises one or more modified pyrimidine and/or purine nucleotides.

22. The pharmaceutical composition according to claim 1, wherein the sense strand of said short interfering nucleic acid molecule targeting the Mcl-1 transcript comprising a terminal cap moiety at the 5'and/or 3'-end(s).

23. The pharmaceutical composition according to claim 1, wherein the antisense strand of said short interfering nucleic acid molecule targeting the Mcl-1 transcript includes a phosphate group at the 5'-end.

24. The pharmaceutical composition according to claim 1, wherein said short interfering nucleic acid molecule targeting the Mcl-1 transcript comprises at least one modified internucleotidic linkage.

* * * * *

UNITED STATES PATENT AND TRADEMARK OFFICE
CERTIFICATE OF CORRECTION

| | | |
|---|---|---|
| PATENT NO. | : 8,193,333 B2 | Page 1 of 1 |
| APPLICATION NO. | : 12/306093 | |
| DATED | : June 5, 2012 | |
| INVENTOR(S) | : Laurent Poulain et al. | |

It is certified that error appears in the above-identified patent and that said Letters Patent is hereby corrected as shown below:

Title Page and Col. 1, in the Title, delete "BCL-$X_l$-SPECIFIC" and replace it with --BCL-$X_L$-SPECIFIC--.

In Claim 22, at column 32, line 45, delete "comprising" and replace it with --comprises--. In addition, at column 32, line 46, add a space between "5'" and "and/or".

Signed and Sealed this
Eleventh Day of September, 2012

David J. Kappos
*Director of the United States Patent and Trademark Office*

SEQUENCE LISTING

```
<160> NUMBER OF SEQ ID NOS: 22

<210> SEQ ID NO 1
<211> LENGTH: 19
<212> TYPE: RNA
<213> ORGANISM: artificial sequence
<220> FEATURE:
<223> OTHER INFORMATION: Bcl-XL mRNA target sequence

<400> SEQUENCE: 1 auggugagu cggaucgca                                                    19

<210> SEQ ID NO 2
<211> LENGTH: 2575
<212> TYPE: DNA
<213> ORGANISM: Homo sapiens
<220> FEATURE:
<221> NAME/KEY: CDS
<222> LOCATION: (367)..(1068)

<400> SEQUENCE: 2
ggaggaggaa gcaagcgagg gggctggttc ctgagcttcg caattcctgt gtcgccttct      60
gggctcccag cctgccgggt cgcatgatcc ctccggccgg agctggtttt tttgccagcc    120
accgcgaggc cggctgagtt accggcatcc ccgcagccac ctcctctccc gacctgtgat    180
```

|  |  |
|---|---|
| acaaaagatc ttccggggggc tgcacctgcc tgcctttgcc taaggcggat ttgaatctct | 240 |
| ttctctccct tcagaatctt atcttggctt tggatcttag aagagaatca ctaaccagag | 300 |
| acgagactca gtgagtgagc aggtgttttg gacaatggac tggttgagcc catccctatt | 360 |

```
ataaaa atg tct cag agc aac cgg gag ctg gtg gtt gac ttt ctc tcc           408
       Met Ser Gln Ser Asn Arg Glu Leu Val Val Asp Phe Leu Ser
         1               5                  10
tac aag ctt tcc cag aaa gga tac agc tgg agt cag ttt agt gat gtg          456
Tyr Lys Leu Ser Gln Lys Gly Tyr Ser Trp Ser Gln Phe Ser Asp Val
 15              20                  25                  30
gaa gag aac agg act gag gcc cca gaa ggg act gaa tcg gag atg gag          504
Glu Glu Asn Arg Thr Glu Ala Pro Glu Gly Thr Glu Ser Glu Met Glu
                 35                  40                  45
acc ccc agt gcc atc aat gga aac cca tcc tgg cac ctg gca gac agc          552
Thr Pro Ser Ala Ile Asn Gly Asn Pro Ser Trp His Leu Ala Asp Ser
                     50                  55                  60
ccc gcg gtg aat gga gcc act ggc cac agc agc agt ttg gat gcc cgg          600
Pro Ala Val Asn Gly Ala Thr Gly His Ser Ser Ser Leu Asp Ala Arg
 65                  70                  75
gag gtg atc ccc atg gca gca gta aag caa gcg ctg agg gag gca ggc          648
Glu Val Ile Pro Met Ala Ala Val Lys Gln Ala Leu Arg Glu Ala Gly
     80                  85                  90
gac gag ttt gaa ctg cgg tac cgg cgg gca ttc agt gac ctg aca tcc          696
Asp Glu Phe Glu Leu Arg Tyr Arg Arg Ala Phe Ser Asp Leu Thr Ser
 95                 100                 105                 110
cag ctc cac atc acc cca ggg aca gca tat cag agc ttt gaa cag gta          744
Gln Leu His Ile Thr Pro Gly Thr Ala Tyr Gln Ser Phe Glu Gln Val
                115                 120                 125
gtg aat gaa ctc ttc cgg gat ggg gta aac tgg ggt cgc att gtg gcc          792
Val Asn Glu Leu Phe Arg Asp Gly Val Asn Trp Gly Arg Ile Val Ala
                    130                 135                 140
ttt ttc tcc ttc ggc ggg gca ctg tgc gtg gaa agc gta gac aag gag          840
Phe Phe Ser Phe Gly Gly Ala Leu Cys Val Glu Ser Val Asp Lys Glu
                145                 150                 155
atg cag gta ttg gtg agt cgg atc gca gct tgg atg gcc act tac ctg          888
Met Gln Val Leu Val Ser Arg Ile Ala Ala Trp Met Ala Thr Tyr Leu
    160                 165                 170
aat gac cac cta gag cct tgg atc cag gag aac ggc ggc tgg gat act          936
Asn Asp His Leu Glu Pro Trp Ile Gln Glu Asn Gly Gly Trp Asp Thr
175                 180                 185                 190
ttt gtg gaa ctc tat ggg aac aat gca gca gcc gag agc cga aag ggc          984
Phe Val Glu Leu Tyr Gly Asn Asn Ala Ala Ala Glu Ser Arg Lys Gly
                    195                 200                 205
cag gaa cgc ttc aac cgc tgg ttc ctg acg ggc atg act gtg gcc ggc         1032
Gln Glu Arg Phe Asn Arg Trp Phe Leu Thr Gly Met Thr Val Ala Gly
                210                 215                 220
gtg gtt ctg ctg ggc tca ctc ttc agt cgg aaa tga ccagacactg              1078
Val Val Leu Leu Gly Ser Leu Phe Ser Arg Lys
                225                 230
```

|  |  |
|---|---|
| accatccact ctaccctccc accccttct ctgctccacc acatcctccg tccagccgcc | 1138 |
| attgccacca ggagaaccac tacatgcagc ccatgcccac ctgcccatca cagggttggg | 1198 |
| cccagatctg gtcccttgca gctagttttc tagaatttat cacacttctg tgagaccccc | 1258 |
| acacctcagt tccttggcc tcagaattca caaaattcc acaaaatctg tccaaaggag | 1318 |
| gctggcaggt atggaagggt tgtggctggg gggcaggagg ccctacctg attggtgcaa | 1378 |
| cccttacccc ttagcctccc tgaaaatgtt tttctgccag ggagcttgaa agttttcaga | 1438 |
| acctcttccc cagaaaggag actagattgc ctttgttttg atgtttgtgg cctcagaatt | 1498 |

```
gatcatttc  cccccactct  ccccacacta  acctgggttc  cctttccttc  catccctacc   1558
ccctaagagc  catttagggg  ccacttttga  ctagggattc  aggctgcttg  ggataaagat   1618
gcaaggacca  ggactccctc  ctcacctctg  gactggctag  agtcctcact  cccagtccaa   1678
atgtcctcca  gaagcctctg  gctagaggcc  agccccaccc  aggagggagg  gggctatagc   1738
tacaggaagc  accccatgcc  aaagctaggg  tggcccttgc  agttcagcac  caccctagtc   1798
ccttcccctc  cctggctccc  atgaccatac  tgagggacca  actgggccca  agacagatgc   1858
cccagagctg  tttatggcct  cagctgcctc  acttcctaca  agagcagcct  gtggcatctt   1918
tgccttgggc  tgctcctcat  ggtgggttca  ggggactcag  ccctgaggtg  aaagggagct   1978
atcaggaaca  gctatgggag  ccccagggtc  ttccctacct  caggcaggaa  gggcaggaag   2038
gagagcctgc  tgcatggggt  ggggtagggc  tgactagaag  ggccagtcct  gcctggccag   2098
gcagatctgt  gccccatgcc  tgtccagcct  gggcagccag  gctgccaagg  ccagagtggc   2158
ctggccagga  gctcttcagg  cctccctctc  tcttctgctc  cacccttggc  ctgtctcatc   2218
cccaggggtc  ccagccaccc  cgggctctct  gctgtacata  tttgagacta  gttttattc    2278
cttgtgaaga  tgatatacta  tttttgttaa  gcgtgtctgt  atttatgtgt  gaggagctgc   2338
tggcttgcag  tgcgcgtgca  cgtggagagc  tggtgcccgg  agattggacg  gcctgatgct   2398
ccctcccctg  ccctggtcca  gggaagctgg  ccgagggtcc  tggctcctga  ggggcatctg   2458
cccctccccc  aaccccccacc  ccacacttgt  tccagctctt  tgaaatagtc  tgtgtgaagg  2518
tgaaagtgca  gttcagtaat  aaactgtgtt  tactcagtga  aaaaaaaaa   aaaaaaa      2575
```

<210> SEQ ID NO 3
<211> LENGTH: 233
<212> TYPE: PRT
<213> ORGANISM: Homo sapiens

<400> SEQUENCE: 3

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190
```

```
Glu Leu Tyr Gly Asn Asn Ala Ala Ala Glu Ser Arg Lys Gly Gln Glu
            195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 4
<211> LENGTH: 19
<212> TYPE: RNA
<213> ORGANISM: artificial sequence
<220> FEATURE:
<223> OTHER INFORMATION: Bcl-XL mRNA target complementary sequence

<400> SEQUENCE: 4
ugcgauccga cucaccaau                                                    19

<210> SEQ ID NO 5
<211> LENGTH: 21
<212> TYPE: DNA
<213> ORGANISM: artificial sequence
<220> FEATURE:
<223> OTHER INFORMATION: siXL1 sense strand

<400> SEQUENCE: 5
auuggugagu cggaucgcat t                                                 21

<210> SEQ ID NO 6
<211> LENGTH: 21
<212> TYPE: DNA
<213> ORGANISM: artificial sequence
<220> FEATURE:
<223> OTHER INFORMATION: siXL1 antisens strand

<400> SEQUENCE: 6
ugcgauccga cucaccaaut t                                                 21

<210> SEQ ID NO 7
<211> LENGTH: 21
<212> TYPE: DNA
<213> ORGANISM: artificial sequence
<220> FEATURE:
<223> OTHER INFORMATION: Mcl-1 siRNA sense strand

<400> SEQUENCE: 7
gugccuuugu ggcuaaacat t                                                 21

<210> SEQ ID NO 8
<211> LENGTH: 21
<212> TYPE: DNA
<213> ORGANISM: artificial sequence
<220> FEATURE:
<223> OTHER INFORMATION: Mcl-1 siRNA antisense strand

<400> SEQUENCE: 8
uguuuagcca caaaggcacc t                                                 21

<210> SEQ ID NO 9
<211> LENGTH: 21
<212> TYPE: DNA
<213> ORGANISM: artificial sequence
<220> FEATURE:
<223> OTHER INFORMATION: control siRNA sense strand

<400> SEQUENCE: 9
```
gacgugggac ugaaggggut t                                              21

<210> SEQ ID NO 10
<211> LENGTH: 21
<212> TYPE: DNA
<213> ORGANISM: artificial sequence
<220> FEATURE:
<223> OTHER INFORMATION: control siRNA antisense strand

<400> SEQUENCE: 10
accccuucag ucccacguct t                                              21

<210> SEQ ID NO 11
<211> LENGTH: 20
<212> TYPE: DNA
<213> ORGANISM: artificial sequence
<220> FEATURE:
<223> OTHER INFORMATION: primer

<400> SEQUENCE: 11
ttggacaatg gactggttga                                                20

<210> SEQ ID NO 12
<211> LENGTH: 19
<212> TYPE: DNA
<213> ORGANISM: artificial sequence
<220> FEATURE:
<223> OTHER INFORMATION: primer

<400> SEQUENCE: 12
gtagagtgga tggtcagtg                                                 19

<210> SEQ ID NO 13
<211> LENGTH: 19
<212> TYPE: DNA
<213> ORGANISM: artificial sequence
<220> FEATURE:
<223> OTHER INFORMATION: primer

<400> SEQUENCE: 13
gtagagtgga tggtcagtg                                                 19

<210> SEQ ID NO 14
<211> LENGTH: 21
<212> TYPE: DNA
<213> ORGANISM: artificial sequence
<220> FEATURE:
<223> OTHER INFORMATION: primer

<400> SEQUENCE: 14
aggtaagtgg ccatccaagc t                                              21

<210> SEQ ID NO 15
<211> LENGTH: 17
<212> TYPE: DNA
<213> ORGANISM: artificial sequence
<220> FEATURE:
<223> OTHER INFORMATION: probe

<400> SEQUENCE: 15
agatgcaggt attggtg                                                   17

<210> SEQ ID NO 16
<211> LENGTH: 20
<212> TYPE: DNA
<213> ORGANISM: artificial sequnce
<220> FEATURE:

```
<223> OTHER INFORMATION: primer

<400> SEQUENCE: 16
gcaccgtcaa ggctgagaac                                           20

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
tctcgctcct ggaagatggt                                           20

<210> SEQ ID NO 18
<211> LENGTH: 20
<212> TYPE: DNA
<213> ORGANISM: artificial sequence
<220> FEATURE:
<223> OTHER INFORMATION: probe

<400> SEQUENCE: 18
tctcgctcct ggaagatggt                                           20

<210> SEQ ID NO 19
<211> LENGTH: 20
<212> TYPE: DNA
<213> ORGANISM: artificial sequence
<220> FEATURE:
<223> OTHER INFORMATION: Mcl-1 siRNA sense strand

<400> SEQUENCE: 19
cugguaguua acaaagatt                                            20

<210> SEQ ID NO 20
<211> LENGTH: 21
<212> TYPE: DNA
<213> ORGANISM: artificial sequence
<220> FEATURE:
<223> OTHER INFORMATION: Mcl-1 siRNA antisense strand

<400> SEQUENCE: 20
ucuuuguuua acuagccagt t                                         21

<210> SEQ ID NO 21
<211> LENGTH: 21
<212> TYPE: DNA
<213> ORGANISM: artificial sequence
<220> FEATURE:
<223> OTHER INFORMATION: Mcl-1 siRNA sense strand

<400> SEQUENCE: 21
gacgauguga aaucguugut t                                         21

<210> SEQ ID NO 22
<211> LENGTH: 21
<212> TYPE: DNA
<213> ORGANISM: artificial sequence
<220> FEATURE:
<223> OTHER INFORMATION: Mcl-1 siRNA antisense strand

<400> SEQUENCE: 22
acaacgauuu cacaucguct t                                         21
```